US011345657B2

(12) United States Patent
Kozelj et al.

(10) Patent No.: US 11,345,657 B2
(45) Date of Patent: May 31, 2022

(54) SULFAMIC ACID DERIVATIVES AND PROCESSES FOR THEIR PREPARATION

(71) Applicant: HYDRO-QUÉBEC, Québec (CA)

(72) Inventors: Matjaz Kozelj, Krka (SI); Catherine Gagnon, Québec (CA); Abdelbast Guerfi, Québec (CA); Karim Zaghib, Québec (CA)

(73) Assignee: HYDRO-QUEBEC, Montreal (CA)

( * ) Notice: Subject to any disclaimer, the term of this patent is extended or adjusted under 35 U.S.C. 154(b) by 262 days.

(21) Appl. No.: 16/343,324

(22) PCT Filed: Oct. 19, 2017

(86) PCT No.: PCT/CA2017/051244
§ 371 (c)(1),
(2) Date: Apr. 18, 2019

(87) PCT Pub. No.: WO2018/072024
PCT Pub. Date: Apr. 26, 2018

(65) Prior Publication Data
US 2020/0181071 A1 Jun. 11, 2020

Related U.S. Application Data

(60) Provisional application No. 62/410,139, filed on Oct. 19, 2016.

(51) Int. Cl.
C07C 303/40 (2006.01)
H01G 11/62 (2013.01)
H01M 10/0525 (2010.01)
H01M 10/0568 (2010.01)
H01M 10/0569 (2010.01)
C07C 307/02 (2006.01)
C07C 311/48 (2006.01)

(52) U.S. Cl.
CPC .......... C07C 303/40 (2013.01); H01G 11/62 (2013.01); H01M 10/0525 (2013.01); H01M 10/0568 (2013.01); H01M 10/0569 (2013.01); C07C 307/02 (2013.01); C07C 311/48 (2013.01)

(58) Field of Classification Search
None
See application file for complete search history.

(56) References Cited

U.S. PATENT DOCUMENTS

| 4,327,034 | A | 4/1982 | Hamprecht et al. |
| 4,499,303 | A * | 2/1985 | Wyrick ................. C07C 307/02 514/605 |
| 4,510,100 | A | 4/1985 | Plattner et al. |
| 5,874,616 | A | 2/1999 | Howells et al. |
| 6,365,301 | B1 | 4/2002 | Michot et al. |
| 8,134,027 | B2 | 3/2012 | Okumura et al. |
| 10,547,084 | B2 | 1/2020 | Schmidt |
| 2004/0014970 | A1 | 1/2004 | Bernard |
| 2005/0159622 | A1 | 7/2005 | Hamprecht et al. |
| 2011/0007086 | A1 | 1/2011 | Na et al. |
| 2011/0034716 | A1 | 2/2011 | Okumura et al. |
| 2011/0070486 | A1 | 3/2011 | Matsumoto et al. |
| 2013/0066110 | A1 | 3/2013 | Honda et al. |
| 2013/0331609 | A1 | 12/2013 | Tsubokura et al. |
| 2014/0075746 | A1 | 3/2014 | Schmidt |
| 2017/0047607 | A1 | 2/2017 | Schmidt et al. |
| 2017/0204124 | A1 | 7/2017 | Takahashi et al. |
| 2018/0039200 | A1 | 2/2018 | Utsuno et al. |
| 2019/0386338 | A1 | 12/2019 | Kawai et al. |

FOREIGN PATENT DOCUMENTS

| CA | 2940037 A1 | 5/2015 |
| CA | 2945872 A1 | 10/2015 |
| CN | 1653043 A | 8/2005 |
| CN | 101747242 A | 6/2010 |
| CN | 102557996 A | 7/2012 |
| CN | 103391896 A | 11/2013 |
| CN | 103562129 A | 2/2014 |
| CN | 104151206 A | 11/2014 |
| EP | 0135927 A2 | 4/1985 |
| EP | 2 578 567 A1 | 4/2013 |
| JP | 50-32145 A | 3/1975 |
| JP | 56-118058 A | 9/1981 |
| JP | S60 105659 A | 6/1985 |
| JP | H41-3452 A | 1/1992 |
| JP | 2005-530794 A | 10/2005 |
| JP | 2010-168249 A | 8/2010 |
| JP | 2014-516907 A | 7/2014 |
| JP | 2016-81796 A | 5/2016 |
| JP | 2016-207313 A | 12/2016 |
| JP | 2018-22074 A | 2/2018 |
| WO | 0240567 A1 | 5/2002 |
| WO | 03035611 A1 | 5/2003 |
| WO | 2009123328 A1 | 10/2009 |
| WO | 2009/136608 A1 | 11/2009 |
| WO | 2011/148958 A1 | 12/2011 |
| WO | 2012/117961 A1 | 9/2012 |
| WO | 2012160280 A2 | 11/2012 |
| WO | 2015/158979 A1 | 10/2015 |
| WO | 2016/002774 A1 | 1/2016 |
| WO | 2016/080384 A1 | 5/2016 |
| WO | 2016/093399 A1 | 6/2016 |
| WO | 2017/179681 A1 | 10/2017 |

OTHER PUBLICATIONS

Appel, et al."Imidobisschwefelsaurechlorid" Chem. Ber. 1962, vol. 95, pp. 625-626.

Haubold, et al.,"Zeitschrift für anorganische und allgemeine Chemie" Z. Anorg. Allg. Chem. 1967, vol. 352, pp. 113-121.

Roesky et al., Darstellung von N-Trifluomethansulfonyl-sulfonylfluoridamid und einige Reaktionen 1" Inorg. Nucl. Chem. Lett. 1971, vol. 7, pp. 171-175.

(Continued)

Primary Examiner — Sudhakar Katakam
Assistant Examiner — Jennifer C Sawyer
(74) Attorney, Agent, or Firm — Buchanan Ingersoll & Rooney P.C.

(57) ABSTRACT

Here are described processes for the preparation of sulfamic acid derivatives, for instance, halogenated derivatives and their metallic or organic salts. The present document also describes the sulfamic acid derivatives thus produced and to their uses, for instance, in electrolyte compositions for electrochemical applications.

30 Claims, 6 Drawing Sheets

(56) References Cited

OTHER PUBLICATIONS

Xu, et al., "A new protonation chemistry of phosphazenes and the formation of bis(sulfonyl)imidesInorg" Chem. Comm. 1999, vol. 2, pp. 261-264.
Appel et al.,"Uber die Reaktion von Chlorsulfonylisocyanat mit Chloroschwefelsaure. Eine neue Synthese des Imidobisschwefelsaurechlorids" Chem. Ber. 1962, vol. 95, pp. 1753-1755.
Appel, et al.Uberdie Reaktion von Sulfuryl-di-isocyanat mit Halogenoschwefelsauren. Ein einfaches Verfahren zur Herstellung vonFluorsulfonylisocyanat und Imido-bis-schwefelsaurefluoridChem. Ber. 1964, vol. 97, pp. 849-851.
Beran, et al."A new route to the syntheses of N-(fluorosulfuryl)sulfonamide salts: Crystal structure of Ph4P + [CF3SO2NSO2F]" Polyhedron, 2010, vol. 29, pp. 991-994.
Beran et al."A New Method of the Preparation of Imido-bis(sulfuric acid) Dihalogenide, (F,CI), and the Potassium Salt of Imido-bis(sulfuric acid) Difluoride" Anorg. Allg. Chem., 2005, vol. 631, pp. 55-59.
Scozzafava, et al."Carbonic Anhydrase Inhibitors: Inhibition of Isozymes I, I1 and IV by Sulfamide and Sulfamic Acid Derivatives" J. Enzyme Inhibition, 2000, vol. 15, pp. 443-453 and "Additions and Corrections" J. Med. Chem. 2001, vol. No. 44, p. 1016.
Baumgarten, et al., Berichte d. D. Chem. Gesellschaft (A and B Series) 1931, vol. 64, pp. 1582-1588.
Gilbert, E. E. "The Reactions of Sulfur Trioxide, and of Its Adducts, With Organic Compounds" Chem. Rev., 1962. vol. 62, No. 6, pp. 549-589.
Kanetani ,et al., Yuki Gosei Kagaku Kyokaishi (J. Synth. Org. Chem. (Japan)), 1974, 32, p. 460-466.
Kanetani ,et al,"Studies of the Reactions of Amines with Sulfur Trioxide. IV. 1, One-step Synthesis of N-substituted Imidobis-sulfates from Amines2", Bull Chem. Soc. Japan, 1974. vol 47, No. 11, pp. 2713-2716.
Bögemann et al."Methoden Der Organischen Chemie" Schwefel-, Selen-, Tellur-Verbindungen. Methoden der organischen Chemie (Houben-Weyl), 4. Auflage, ed. E. Müller. vol. IX. 1955, Georg Thieme: Stuttgart, 26 pages.
Vogel, Vogel's Textbook of Practical Organic Chemistry. 5th ed1989, London: Longman Group, Ltd., p. 1284.
Blotny, G. "A new, mild preparation of sulfonyl chlorides" Tetrahedron Letters, 2003, vol. 44, No. 7, pp. 1499-1501.
Olah, et al.,"Organic Fluorine Compounds. XXVII.1 Preparation of Acyl Fluorides with Anhydrous Hydrogen Fluoride. The general Use of the Method of Colson and Fredenhagen" J. Org. Chem., 1961, vol. 26, No. 1, pp. 237-238.
Olah, et al.,"Synthetic Methods and Reactions;1 Fluorination of Carboxylic Acid with Cyanuric Fluoride" Synthesis, 1973, pp. 487-488.
Olah, et al.,"126. Georg Olhh, Stefan Kuhn und Stefan Beke: Darstellung und Untersuchung organischer Fluorverbindungen XXQ. Darstellung von Siiurefluoriden*)" Chem. Ber., 1956, vol. 89, No. 4, pp. 862-864.
Olah, et al., "Synthetic Methods and Reactions. 63.' Pyridinium Poly( hydrogen fluoride) (30% Pyridine-70% Hydrogen Fluoride): A Convenient Reagent for Organic Fluorination Reactions" J. Org. Chem., 1979, vol. 44, No. 22, pp. 3872-3881.
Hudlicky, Fluorination with Diethylaminosulfur Trifluoride and Related Aminofluorosulfuranes Chapter 3, Org. Reactions, 1988. vol. 35, pp. 513-637.
Hillebrecht, A. et al. "Integrated Approach Using Protein and Ligand Information to Analyze Selectivity- and Affinity-Determining Features of Carbonic Anhydrase Isozymes" Wiley VCH Verlag GmbH & Co. KGaA, Weinheim, ChemMedchem, 2006, vol. 1, pp. 839-853.
Koppel, I. A. et al. "Generalized Principle of Designing Neutral Superstrong Bronsted Acids" J. Am. Chem. Soc. 2002, vol. 124, pp. 5594-5600.
Burk, P. et al."Superacidity of Neutral Brönsted Acids in Gas Phase" Journal of Computational Chemistry, vol. 17, No. 1, 12 pages.
Kubota, K. et al."Investigation of an Intermediate Temperature Molten Lithium Salt Based on Fluorosulfonyl (trifluoromethylsulfonyl)amide as a Solvent-Free Lithium Battery Electrolyte" The Journal of Physical Chemistry, 8 pages.
Extended European Search Report dated May 12, 2020, issued by the European Patent Office in corresponding European Application No. 17861268.5-1109, (23 pages).
Kanetani, F."Preparation of Arylimidobis(sulfates)" Bull. Chem. Soc. vol. 59, No. 3, 1985, pp. 952-954.
Office Action (Notice of Reasons for Rejection) dated Aug. 31, 2021 by the Japanese Patent Office in corresponding Japanese Patent Application No. 2019-520726, and an English Translation of the Office Action. (21 pages).
International Search Report (PCT/ISA/210) dated Jan. 15, 2018, by the Canadian Patent Office as the International Searching Authority for International Application No. PCT/CA2017/051244.
Written Opinion (PCT/ISA/237) dated Jan. 15, 2018, by the Canadian Patent Office as the International Searching Authority for International Application No. PCT/CA2017/051244.
Office Action (Text of the First Office Action) dated May 24, 2021, by the Chinese Patent Office in corresponding Chinese Patent Application No. 201780062337.7, and an English Translation of the Office Action (25 pages).
Office Action (the Second Office Action) dated Dec. 14, 2021, by the State Intellectual Property Office of the People's Republic of China in corresponding Chinese Patent Application No. 201780062337.7, and an English Translation of the Office Action. (17 pages).

* cited by examiner (a)

(b)

(a)

(b)

(a)

(b)

SULFAMIC ACID DERIVATIVES AND PROCESSES FOR THEIR PREPARATION

RELATED APPLICATION

The present application claims priority, under applicable law, to U.S. provisional application No. 62/410,139 filed on Oct. 19, 2016, the content of which incorporated herein by reference in its entirety and for all purposes.

TECHNICAL FIELD

The technical field generally relates to processes for the preparation of sulfamic acids derivatives, for instance, halogenated derivatives and their salts, including ionic liquids. The technical field also relate to these sulfamic acid derivatives and to their use in electrolytes for electrochemical applications.

BACKGROUND

Some sulfamic acid derivatives, due to their unique properties, gained importance in electrochemical applications. Examples of such compounds include bis(fluorosulfonyl)amide, N-fluorosulfonyl(trifluoromethanesulfonyl)amide and their salts, especially their lithium salts (commonly called LiFSI and LiFTFSI). Their unique properties include good solubility, electrochemical stability and ability to lower the viscosity and melting temperature of ionic liquids, i.e. when these fluorosulfonylamides are used as anions in ionic liquids (see U.S. Pat. Nos. 6,365,301, 5,874,616, and US 2011/007086).

Known methods for their preparation include the reaction of halosulfuric acids with isocyanates, sulfinylamines and phosphazenes. However, these methods are time consuming, typically requiring reaction times over 20 hours to ensure a good conversion.

The reaction of various amides with phosphorus pentachloride yielding trichlorophosphazenes, which can in turn be reacted with various acids to produce new disubstituted amides, especially bis(fluorosulfonyl)amide and N-fluorosulfonyl-(trifluoromethanesulfonyl)amide have been previously described (see R. Appel et al., *Chem. Ber.* 1962, 95, 625-626; W. Haubold et al., *Z. Anorg. Alig. Chem* 1967, 352, 113-121; V. H. W. Roesky et al., *Inorg. Nucl. Chem. Lett.* 1971, 7, 171-175; and K. Xu et al., *Inorg. Chem. Comm.* 1999, 2, 261-264). The main disadvantage of these is the use of highly corrosive and toxic phosphorus compounds and the required separation of desired products from their by-products.

R. Appel et al., Chem. Ber. 1962, 95, 1753-1755; R. Appel et al., *Chem. Ber.* 1964, 97, 849-851; and U.S. Pat. No. 8,134,027, described reactions of acids with chlorosulfonyl isocyanate. The products obtained are chlorosulfonyl substituted amides. However, prolonged reaction times, i.e. over 24 h in some cases, are needed to complete the reactions.

The reaction of amides with $SO_2Cl_2$ and chlorosulfonic acid typically generates amides substituted with chlorosulfonyl groups, and this, also after 24 h hours under reflux (see see M. Beran et al., *Z. Anorg. Allg. Chem.*, 2005, 631, 55-59; M. Beran et al., *Polyhedron* 2010, 29, 991-994; and Chinese patent application No. 10174724).

US application published under No. 2011/0070486 describes the preparation of N-fluorosulfonyl(trifluoromethanesulfonyl)amide by acylation of potassium trifluoromethanesulfonimide with non-commercially available fluorosulfonic anhydride. U.S. Pat. No 5,874,616 describes the preparation, at low temperatures, of N-fluorosulfonyl-(trifluoromethanesulfonyl)amide by acylation of trifluoromethanesulfonylamide using highly toxic sulfuryl fluoride, which makes the method inappropriate when a larger scale production is contemplated.

On the other hand, acylation of sulfamic acid was also used to prepare various N-sulfonyl sulfamic acids (see Scozzafava, A. et al., *J. Enz. Inhib.*, 2000, 15(5), 443-453). However, the publication only reports the preparation of substituted sulfamic acid and some salts.

All of the aforementioned methods require long reaction times, and are thus not adapted for cost efficient production.

Sulfonation of non-halogenated (more reactive) amides with the pyridinium-sulfur trioxide complex were also described in P. Baumgarten, et al., *Berichte d. D. Chem. Gesellschaft (A and B Series)* 1931, 64, 1582-1588. Other sulfur trioxide complexes were also prepared and used in sulfonations, such as those reviewed in Gilbert, E. E., *Chem. Rev.*, 1962. 62(6): p. 549-589.

A group also studied the preparation of various sulfamic acid derivatives by sulfonation of amines and amidosulfates using sulfur trioxide complexes (see Kanetani, F. et al., *Yuki Gosei Kagaku Kyokaishi (J. Synth. Org. Chem.* (Japan)), 1974. 32, p. 460-466, and Kanetani, F. et al, *Bull. Chem. Soc. Jap.*, 1974. 47(11), p. 2713-2716). The further transformation of these derivatives into halogenated sulfamic acid derivatives was not described.

Preparation of sulfonyl chlorides from sulfonic acid salts is known to organic chemists (e.g., see Bögemann, M. et al., eds. *Schwefel-, Selen-, Tellur-Verbindungen. Methoden der organischen Chemie (Houben-Weyl)*, 4. Auflage, ed. E. Müller. Vol. IX. 1955, Georg Thieme: Stuttgart, pp 391-394, 561-597; Vogel, A., *Vogel's Textbook of Practical Organic Chemistry.* 5$^{th}$ ed 1989, London: Longman Group, Ltd., pp 1284; and Blotny, G., *Tetrahedron Letters*, 2003. 44(7): p. 1499-1501).

Preparation of sulfonyl fluorides was also described in Olah, G. et al., *J. Org. Chem.*, 1961. 26(1): p. 237-238.; Olah, G. A. et al., *Synthesis*, 1973: p. 487-488.; Oláh, G. et al., *Chem. Ber.*, 1956. 89(4): p. 862-864; and Olah, G. A., et al., *J. Org. Chem.*, 1979. 44(22): p. 3872-3881. Several compounds were also prepared from sulfur fluorides (see Hudlicky, M., *Org. Reactions*, 1988. 35: p. 513-637).

Therefore, it is highly desirable to develop an improved process for the production of sulfamic acid derivatives.

SUMMARY

According to one aspect, here is described a process for the preparation of a sulfamic acid derivative, or a salt thereof with one or more metallic or organic cations. For instance, the sulfamic acid derivative is defined according to Formula I:

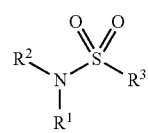

Formula I wherein, $R^1$ is selected from hydrogen and a linear or branched $C_1$-$C_{24}$alkyl, a $C_6$-$C_{10}$aryl or a $C_5$-$C_{10}$heteroaryl group, the alkyl, aryl and heteroaryl groups being optionally halogenated, or $R^1$ and the adjacent nitrogen atom together form a salt wherein the nitrogen atom is negatively charged (anion) and $R^1$ is $(M^{n+})_{1/n}$ or $X^+$;

$R^2$ is selected from hydrogen, cyano, sulfonyl, chlorosulfonyl, fluorosulfonyl, chlorocarbonyl, fluorocarbonyl, optionally halogenated linear or branched $C_1$-$C_{24}$alkanoyl, optionally halogenated aryloyl, optionally halogenated heteroaryloyl, optionally halogenated linear or branched $C_1$-$C_{24}$alkanesulfonyl, optionally halogenated arylsulfonyl, and optionally halogenated heteroarylsulfonyl;

$R^3$ is selected from OH, F, Cl, $O^-(M^{n+})_{1/n}$, $O^-X^+$, and optionally halogenated linear or branched $C_1$-$C_{24}$alkoxy;

$(M^{n+})_{1/n}$ is a metal cation, wherein M is a metal and n is an integer selected from 1 to 4, for instance, M is Li, Na, K, Rb, Cs, Be, Mg, Ca, Sr, Ba, Al, Zn, Cu, Sc, Y, Fe, Co, Ni, Ti, Sn, V, Cr, or Mn, for example, M is selected from Li, Na, K, Rb, Cs, Be, Mg, Ca, Sr, Ba, Al, Zn, Sc, and Ti, for instance M is an alkali metal, alkaline earth metal, or aluminum, or M is selected from Li, Na, K, Rb, Cs, Be, Mg, Ca, Sr, and Ba, and n is 1 or 2; and $X^+$ represents an organic cation, for instance, selected from ammonium, alkylammonium, dialkylammonium, trialkylammonium, tetraalkylammonium, 1,3-dialkylimidazolium, N-alkylpyrrolidinium, N-alkylpiperidinium, trialkyloxonium, trialkylsulfonium, tetraalkylphosphonium, and the like;

the process comprising the steps of:
i) contacting a compound of the formula:

with a sulfur trioxide source and a tertiary amine and heating at a temperature comprised between about 50° C. and about 300° C.; and ii) optionally converting the product obtained in step (i) to produce a compound of Formula I.

When the above compound, or any other compound described in the present document, is in the form of a salt, then the ratio of anion to cation is understood as aiming for the electroneutrality of the compound (for example, two sulfamic acid derivatives of a −1 charge may be required when a magnesium $Mg^{2+}$ cation is used, similarly, two lithium (+1) cations may be combined to a dianion of a sulfamic acid derivative).

According to one embodiment, the sulfur trioxide source is selected from $SO_3$ (sulfur trioxide itself) and its oligomers and polymers; $H_2SO_4$ (sulfuric acid); $H_2S_2O_7$ (disulfuric acid) and other polysulfuric acids and their salts; $ClSO_3H$ (chlorosulfonic acid) and its salts; $FSO_3H$ (fluorosulfonic acid) and its salts; $SO_3$-ammonia complex (sulfamic acid); complexes of sulfur trioxide with organic amines; complexes of sulfur trioxide with other organic compounds such as dioxane, thioxane, dimethylformamide; and acylsulfates, which are generated by introduction of $SO_3$ into dry carboxylic acids, for example, acetyl sulfate ($CH_3C(O)OSO_3H$).

In another embodiment, the sulfur trioxide source and the tertiary amine are added together as a complex, and the tertiary amine is selected from the following compounds: trimethylamine, triethylamine, tripropylamine, tributylamine, diisopropylethylamine, N-alkyl substituted pyrrolidines and morpholines, pyridine, picoline, lutidine, quinoline, N,N-dimethylaniline, and other amines. For instance, the complex is selected from pyridine-sulfur trioxide, trimethylamine-sulfur trioxide and triethylamine-sulfur trioxide complexes.

In another embodiment, step (i) comprises heating at a temperature of between about 100° C. and about 250° C., or between about 150° C. and about 220° C., for instance, for a period of less than 10 hours, less than 4 hours, or less than 1 hour. According to one embodiment, step (i) is carried out without addition of a solvent.

According to a further embodiment, the process comprises step (ii) which includes contacting the product obtained in step (i) with a metallic base. For example, the metallic base is selected from metal hydroxides, metal alkoxides, organometallics and Grignard reagents, said metal being selected from alkali metals, alkaline earth metals, and aluminum, for instance, the metallic base is a metal hydroxide.

In another embodiment, the process further comprises a step of treating the product of step (i) or of step (ii) with a strong acid or passing a solution thereof through an acidic ion exchange resin. For instance, the strong acid is selected from hydrochloric acid, hydrobromic acid, sulfuric acid, nitric acid, and trifluoromethanesulfonic acid.

In a further embodiment, the process comprises step (ii) which includes contacting the product obtained in step (i) with a chlorinating agent. For example, the chlorinating agent is selected from inorganic and organic acid chlorides, such as $PCl_5$, $POCl_3$, $SOCl_2$, $ClSO_3H$, $COCl_2$, $ClCOCOCl$, sulfur chlorides, cyanuric chloride, acetyl chloride, trifluoroacetyl chloride, methanesulfonyl chloride, trifluoromethanesulfonyl chloride, benzoyl chloride, (trichloromethyl)benzene, benzenesulfonyl chloride, toluenesulfonyl chloride and the like, for instance, the chlorinating agent is $SOCl_2$, $COCl_2$, or $ClCOCOCl$. In yet another embodiment, the process further comprises a step of contacting the product obtained in step (ii), after chlorination, with a fluorinating agent. For instance, the fluorinating agent is selected from fluoride or hydrogen difluoride salts (such as an ammonium, sodium, potassium, or cesium salt, e.g. KF or $KHF_2$), and a complex salt of amines and hydrofluoric acid (like pyridinium or triethylammonium polyhydrofluorides).

In a further embodiment, the process comprises step (ii) which includes contacting the product obtained in step (i) with a strong fluorinating agent. In another embodiment, the fluorinating agent is selected from reactive inorganic and organic acid fluorides, such as $PF_5$, $POF_3$, $SOF_2$, $FSO_3H$, $COF_2$, FCOCOF, organic and inorganic hexafluorophosphates, hexafluorosilicates, tetrafluoroborates, sulfur tetrafluoride and organic derivatives (like diethylaminosulfur trifluoride (DAST) and morpholinosulfur trifluoride), cyanuric fluoride, acetyl fluoride, trifluoroacetyl fluoride, methanesulfonyl fluoride, trifluoromethanesulfonyl fluoride, benzoyl fluoride, (trifluoromethyl)benzene, benzenesulfonyl fluoride, toluenesulfonyl fluoride and the like.

According to another aspect, this relates to a sulfamic acid derivative prepared by a process as herein described. In one embodiment, the sulfamic acid derivative is defined by Formula I:

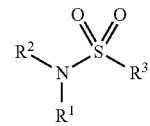

Formula I wherein,
$R^1$ is selected from hydrogen and linear or branched $C_1$-$C_{24}$alkyl, $C_6$-$C_{10}$aryl or $C_5$-$C_{10}$heteroaryl groups, the alkyl, aryl and heteroaryl groups being optionally halogenated, or $R^1$ and the adjacent nitrogen atom together form a salt wherein the nitrogen atom is negatively charged (anion) and $R^1$ is $(M^{n+})_{1/n}$ or $X^+$;

$R^2$ is selected from hydrogen, cyano, sulfonyl, chlorosulfonyl, fluorosulfonyl, chlorocarbonyl, fluorocarbonyl, optionally halogenated linear or branched $C_1$-$C_{24}$alkanoyl, optionally halogenated aryloyl, optionally halogenated heteroaryloyl, optionally halogenated linear or branched $C_1$-$C_{24}$alkanesulfonyl, optionally halogenated arylsulfonyl, and optionally halogenated heteroarylsulfonyl;

$R^3$ is selected from OH, F, Cl, $O^-(M^{n+})_{1/n}$, $O^-Z^+$, and an optionally halogenated linear or branched $C_1$-$C_{24}$alkoxy;

$(M^{n+})_{1/n}$ is a metal cation, wherein M is a metal and n is an integer selected from 1 to 4, for instance, M is Li, Na, K, Rb, Cs, Be, Mg, Ca, Sr, Ba, Al, Zn, Cu, Sc, Y, Fe, Co, Ni, Ti, Sn, V, Cr, or Mn, for example, M is selected from Li, Na, K, Rb, Cs, Be, Mg, Ca, Sr, Ba, Al, Zn, Sc, and Ti, for instance M is an alkali metal, alkaline earth metal, or aluminum, or M is selected from Li, Na, K, Rb, Cs, Be, Mg, Ca, Sr, and Ba, and n is 1 or 2; and $X^+$ represents an organic cation, for instance, selected from ammonium, alkylammonium, dialkylammonium, trialkylammonium, tetraalkylammonium, 1,3-dialkylimidazolium, N-alkylpyrrolidinium, N-alkylpiperidinium, trialkyloxonium, trialkylsulfonium, tetraalkylphosphonium and the like.

In one embodiment, $R^1$ is $(M^{n+})_{1/n}$ where M is selected from Li, Na, K, Rb, Cs, Be, Mg, Ca, Sr, Ba, Al, Zn, Cu, Sc, Y, Fe, Co, Ni, Ti, Sn, V, Cr, and Mn. In another embodiment, M is selected from Li, Na, K, Rb, Cs, Be, Mg, Ca, Sr, Ba, Al, Zn, Sc, and Ti, or M is Li, Na or K.

In another embodiment, $R^1$ is $X^+$ and is selected from ammonium, alkylammonium, dialkylammonium, trialkylammonium, tetraalkylammonium, 1,3-dialkylimidazolium, N-alkylpyrrolidinium, N-alkylpiperidinium, trialkyloxonium, trialkylsulfonium, tetraalkylphosphonium ions and other similar ions. In some cases, a salt including an organic cation may be liquid at room temperature, thereby forming an ionic liquid.

In one embodiment, $R^2$ is selected from the groups chlorosulfonyl, fluorosulfonyl, chlorocarbonyl, fluorocarbonyl, linear or branched $C_1$-$C_{24}$alkanoyl, perfluorinated linear or branched $C_1$-$C_{24}$alkanoyl, linear or branched $C_1$-$C_{24}$alkanesulfonyl, and perfluorinated linear or branched $C_1$-$C_{24}$alkanesulfonyl, all other groups being as herein defined.

In a further embodiment, the sulfamic acid derivative is a compound of Formula II:

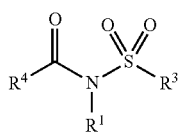

Formula II wherein $R^1$ and $R^3$ are as previously defined; and $R^4$ is selected from hydrogen, cyano, fluorine, chlorine, and a linear or branched $C_1$-$C_{24}$alkyl, $C_6$-$C_{10}$aryl or $C_5$-$C_{10}$heteroaryl group, each being optionally halogenated.

In another embodiment, the sulfamic acid derivative is a compound of Formula III:

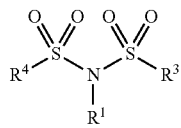

Formula III wherein $R^1$, $R^3$, and $R^4$ are as previously defined.

In one embodiment, $R^4$ in Formula II or III is selected from fluorine, chlorine, and a linear or branched $C_1$-$C_{24}$alkyl, all other groups being as herein defined. In another embodiment, $R^4$ is a perfluorinated linear or branched $C_1$-$C_{24}$alkyl, perfluorinated $C_6$-$C_{10}$aryl, or perfluorinated $C_5$-$C_{10}$heteroaryl group, for instance, a perfluorinated linear $C_1$-$C_{24}$alkyl group, all other groups being as herein defined.

In another embodiment, according to any one of the above formulae, $R^1$ is $M^{n+}_{1/n}$ wherein M is selected from Li, Na, K, Rb, Cs, Be, Mg, Ca, Sr, Ba, and Al, all other groups being as herein defined. Alternatively, $R^1$ is selected from a linear or branched $C_1$-$C_{24}$alkyl, a $C_6$-$C_{10}$aryl and a $C_5$-$C_{10}$heteroaryl, each being an optionally perhalogenated, for instance, $R^1$ is a perhalogenated linear or branched $C_1$-$C_{24}$alkyl, such as a perfluorinated linear or branched $C_1$-$C_{24}$alkyl, all other groups being as herein defined.

In yet another embodiment, $R^1$ is $(M^{n+})_{1/n}$ and $R^3$ is $O^-(M^{n+})_{1/n}$, wherein M and n are the same in each instance and are as herein defined, for instance, M is selected from Li, Na, K, Rb, Cs, Be, Mg, Ca, Sr, and Ba, and n is 1 or 2, or M is Li and n is 1, the other groups being as herein defined. In a further embodiment, $R^3$ is F or Cl, the other groups being as herein defined.

This document also refers to a sulfamic acid derivative selected from Compounds 1 to 9, Compounds 10 to 18, Compounds 19 to 27, or Compounds 28 to 36, as defined below.

The present technology also further relates to an electrolyte or electrolyte composition comprising a sulfamic acid derivative prepared by a process of the present document, or as defined herein. For instance, the electrolyte may further comprise a solvent or solvating polymer suitable for preparing polymer electrolytes. The electrolyte may be in liquid or gel form, optionally including a separator (membrane), or in solid form.

Also contemplated are electrochemical cells comprising an electrolyte as defined herein, an electrode and a counter-electrode, for example, a battery, an electrochromic device, or a capacitor. According to one example, the battery is a lithium or lithium-ion battery. The use of these electrochemical cells in electric or hybrid vehicles, or in computing and/or telecommunications devices is also contemplated.

Although the above compounds may be useful in electrochemistry, other uses, such as chemical catalysis, may also be contemplated.

Other features of the present technology will be better understood upon reading the herein below description.

DETAILED DESCRIPTION

Figure 1:
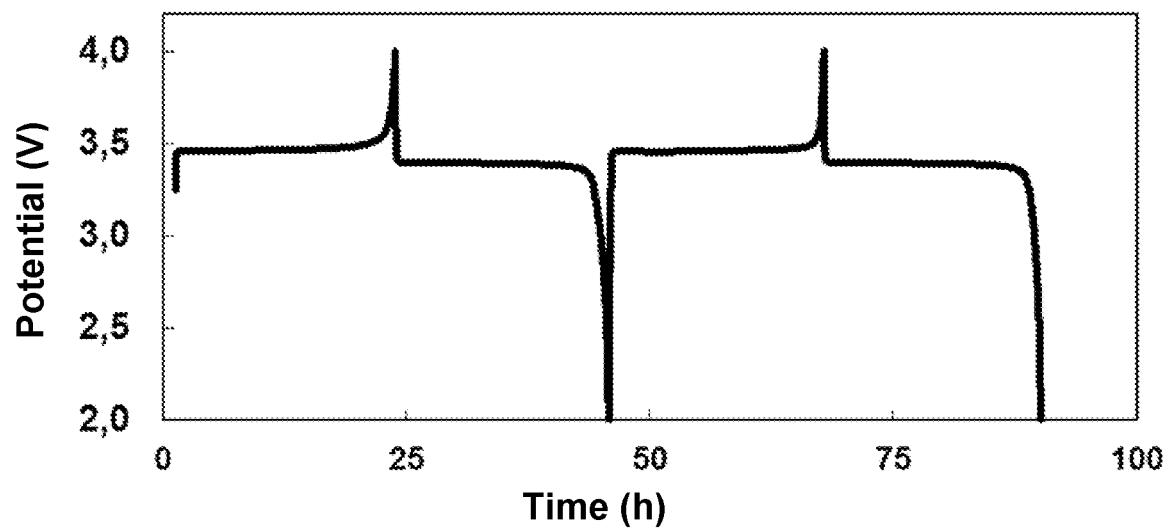
FIG. 1 presents the potential as a function of time at the formation step in a cell or half-cell using an electrolyte containing LiFSI produced by the present process respectively with (a) LiFePO$_4$ and (b) graphite as electrode material, according to Example 13.
Figure 1:
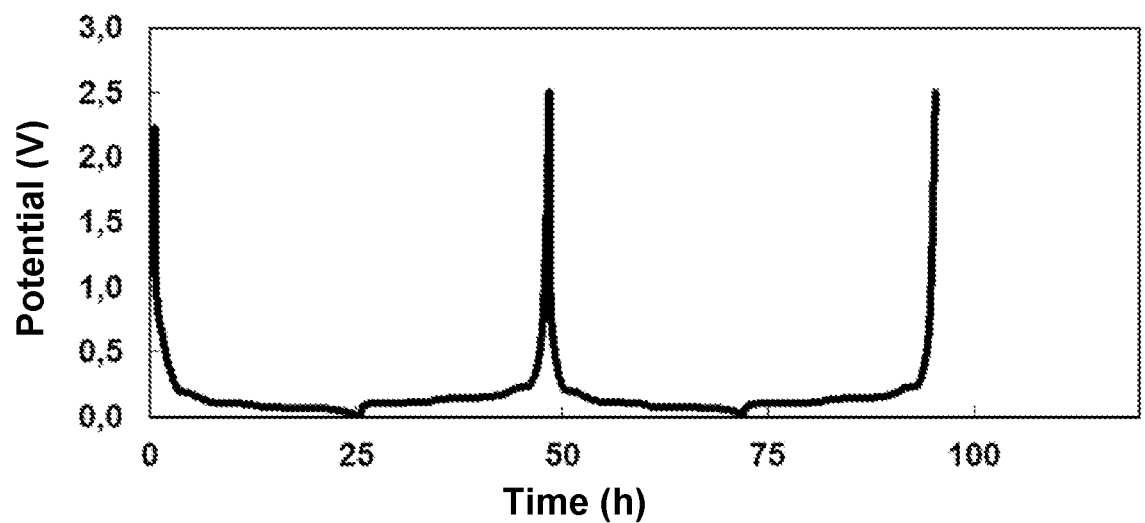

All technical and scientific terms and expressions used herein have the same definitions as those commonly understood by the person skilled in the art relating to the present technology. The definition of some terms and expressions used herein is nonetheless provided below.

The term "about" as used in the present document means approximately, in the region of, and around. When the term "about" is used in relation to a numerical value, it modifies it, for example, above and below by a variation of 10% related to its nominal value. This term may also take into account, for instance, the experimental error of a measuring device or rounding.

When a range of values is mentioned in the present application, the lower and upper limits of the range are, unless otherwise indicated, always included in the definition.

The chemical structures described herein are drawn according to standards of the field. Also, when an atom, such as a carbon atom, as drawn seems to include an incomplete valency, then the valency is assumed to be satisfied by one or more hydrogen atoms even if they are not explicitly drawn.

As used herein, the term "alkyl" refers to a saturated hydrocarbon group having between one and twenty-four carbon atoms, including linear or branched groups. Examples of alkyl groups comprise, without limitation, methyl, ethyl, propyl, butyl, pentyl, hexyl, heptyl, octyl, nonyl, decyl, isopropyl, tert-butyl, sec-butyl, isobutyl, and the like. The term "C$_i$-C$_{ii}$alkyl" refers to an alkyl group having from the number "i" to the number "ii" of carbon atom(s).

As used herein, the term "aryl" refers to an aromatic group having 4n+2 π(pi) electrons, where n is an integer of from 1 to 3, in a monocyclic or polycyclic (fused or not) conjugated system and having from six to fourteen cycle atoms. A polycyclic system includes at least one aromatic cycle. The group may be directly linked or connected via a C$_1$-C$_3$alkyl group. Examples of aryl groups include, without limitation, phenyl, benzyl, phenethyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthrenyl, anthracenyl, perylenyl, and the like. The term aryl includes substituted or unsubstituted groups. For example, the term "C$_6$-C$_n$aryl" refers to an aryl group having from 6 to an indicated number "n" of carbon atoms in the cyclic structure.

As used herein, the term «heteroaryl» refers to an aryl group having 4n+2 π(pi) electrons, where n is an integer of from 1 to 3, in a monocyclic or polycyclic conjugated system and having from five to fourteen cycle atoms, and wherein at least one carbon atom is replaced by a heteroatom such as nitrogen, oxygen or sulfur, or by a group comprising such heteroatom (for example, NH, NR$_x$, (R$_x$ being alkyl, acyl, aryl, heteroaryl or cycloalkyl), SO, and other similar groups). A polycyclic system includes at least one heteroaromatic cycle. Heteroaryls may be directly connected or though a C$_1$-C$_3$alkyl group. Heteroaryl groups may be connected to the rest of the molecule by a carbon atom or by a heteroatom, (such as nitrogen), when possible.

The present application relates to a process for the preparation of sulfamic acid derivatives, for example, a compound of Formula I:

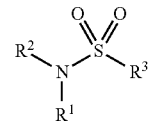

Formula I wherein,

R$^1$ is selected from hydrogen and linear or branched C$_1$-C$_{24}$alkyl, C$_6$-C$_{10}$aryl or C$_5$-C$_{10}$heteroaryl groups, each being optionally halogenated, or R$^1$ and the adjacent nitrogen atom form together a salt wherein the nitrogen atom is negatively charged (anion) and R$^1$ is (M$^+$)$_{1/n}$ or X$^+$;

R$^2$ is selected from hydrogen and the groups cyano, sulfonyl, chlorosulfonyl, fluorosulfonyl, chlorocarbonyl, fluorocarbonyl, optionally halogenated linear or branched C$_1$-C$_{24}$alkanoyl, optionally halogenated aryloyl, optionally halogenated heteroaryloyl, optionally halogenated linear or branched C$_1$-C$_{24}$alkanesulfonyl, optionally halogenated arylsulfonyl, and optionally halogenated heteroarylsulfonyl;

R$^3$ is selected from OH, F, Cl, O$^-$(M$^{n+}$)$_{1/n}$, O$^-$X$^+$, and an optionally halogenated linear or branched C$_1$-C$_{24}$alkoxy, for example, optionally halogenated linear or branched C$_1$-C$_8$alkoxy;

(M$^{n+}$)$_{1/n}$ is a metal cation, wherein M is a metal and n is an integer selected within the range of from 1 to 4, for instance, M is Li, Na, K, Rb, Cs, Be, Mg, Ca, Sr, Ba, Al, Zn, Cu, Sc, Y, Fe, Co, Ni, Ti, Sn, V, Cr, or Mn, for example, M is selected from Li, Na, K, Rb, Cs, Be, Mg, Ca, Sr, Ba, Al, Zn, Sc, and Ti, for instance M is an alkali metal, alkaline earth metal, or aluminum, or M is selected from Li, Na, K, Rb, Cs, Be, Mg, Ca, Sr, and Ba, and n is 1 or 2, or M is Li and n is 1; and X$^+$ represents an organic cation, for instance, selected from ammonium, alkylammonium, dialkylammonium, trialkylammonium, tetraalkylammonium, 1,3-dialkylimidazolium, N-alkylpyrrolidinium, N-alkylpiperidinium, trialkyloxonium, trialkylsulfonium, tetraalkylphosphonium, and other similar organic cations.

According to one example, at least one of R$^1$, R$^2$ and R$^3$ is halogenated. R$^1$ may be selected from hydrogen and the groups linear or branched C$_1$-C$_8$alkyl, C$_6$aryl and C$_5$-C$_6$heteroaryl, each being optionally halogenated. According to another example, R$^1$ and the adjacent nitrogen atom form together a salt wherein the nitrogen atom is negatively charged (anion) and $R^1$ is $(M^{n+})_{1/n}$. According to a different example, $R^1$ and the adjacent nitrogen atom form together a salt wherein the nitrogen atom is negatively charged (anion) and $R^1$ is $X^+$.

According to another example, $R^2$ is selected from perfluorinated linear or branched $C_1$-$C_{24}$alkanoyl, perfluorinated aryloyl, perfluorinated heteroaryloyl, perfluorinated linear or branched $C_1$-$C_{24}$alkanesulfonyl, perfluorinated arylsulfonyl, and perfluorinated heteroarylsulfonyl groups. In some examples, the perfluorinated $C_1$-$C_{24}$alkanoyl or $C_1$-$C_{24}$alkanesulfonyl group is linear.

In another example, $R^2$ is selected from perfluorinated linear or branched $C_1$-$C_8$alkanoyl, perfluorinated $C_6$aryloyl, perfluorinated $C_5$-$C_6$heteroaryloyl, perfluorinated linear or branched $C_1$-$C_8$alkanesulfonyl, perfluorinated $C_6$arylsulfonyl, and perfluorinated $C_5$-$C_6$heteroarylsulfonyl groups. In some examples, the perfluorinated $C_1$-$C_8$alkanoyl or $C_1$-$C_8$alkanesulfonyl group is linear.

According to another example, the sulfamic acid derivative is a compound of Formula II or III:

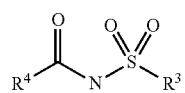

Formula II

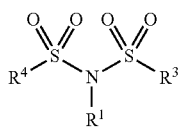

Formula III wherein, $R^1$ and $R^3$ are as previously defined; and $R^4$ is selected from hydrogen, cyano, fluorine, chlorine, and branched or linear $C_1$-$C_{24}$alkyl, $C_6$-$C_{10}$aryl or $C_5$-$C_{10}$heteroaryl groups, each being optionally halogenated.

According to another embodiment, at least one of $R^3$ and $R^4$ is a halogen, i.e. a fluorine or chlorine atom and all other groups are as previously defined. For example, $R^3$ is a halogen, i.e. a fluorine or chlorine atom.

According to one alternative, $R^4$ is selected from linear or branched $C_1$-$C_{24}$alkyl, $C_6$-$C_{10}$aryl or $C_5$-$C_{10}$heteroaryl groups, each being optionally halogenated. For example, $R^4$ is selected from perfluorinated linear or branched $C_1$-$C_{24}$alkyl, perfluorinated $C_6$-$C_{10}$aryl, and perfluorinated $C_5$-$C_{10}$heteroaryl. In some examples, the perfluorinated $C_1$-$C_{24}$alkyl group is linear.

According to one alternative, $R^4$ is selected from linear or branched $C_1$-$C_8$alkyl, $C_6$aryl or $C_5$-$C_6$heteroaryl groups, each being optionally halogenated. For example, $R^4$ is selected from perfluorinated linear or branched $C_{1-8}$alkyl, perfluorinated $C_6$aryl, and perfluorinated $C_5$-$C_6$heteroaryl. In some examples, the perfluorinated $C_1$-$C_8$alkyl group is linear.

Examples of sulfamic acid derivatives include, without limitation, the following compounds:

Compound 1

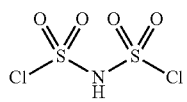

Compound 2

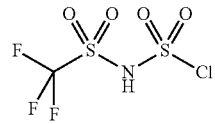

Compound 3

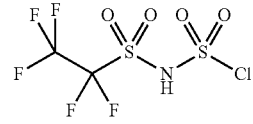

Compound 4

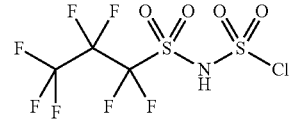

Compound 5

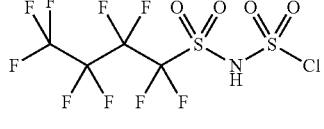

Compound 6

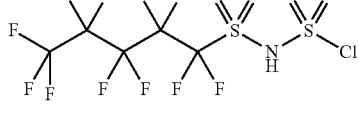

Compound 7

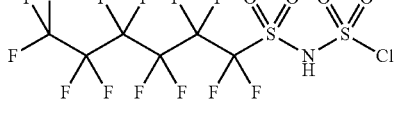

Compound 8

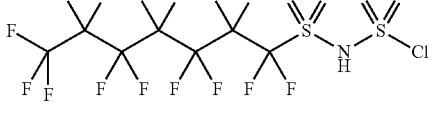

Compound 9

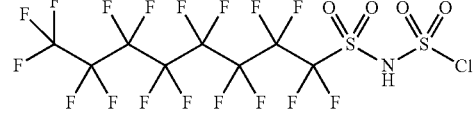

Compound 10

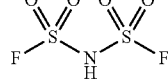

Compound 11

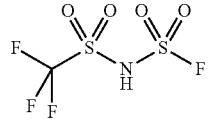

Compound 12

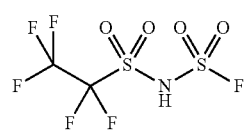

Compound 13

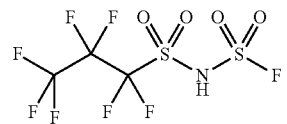

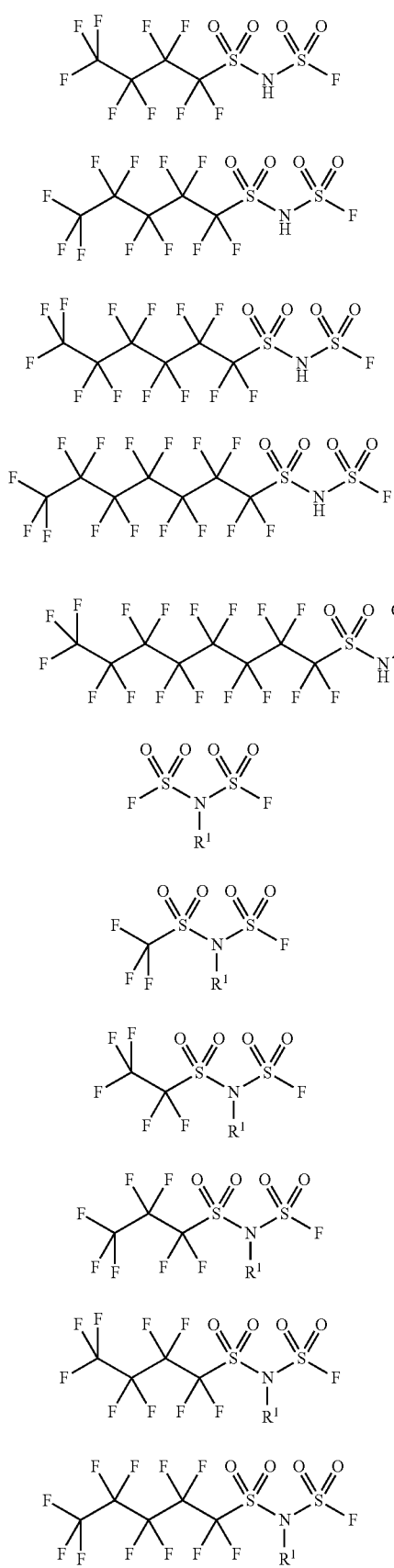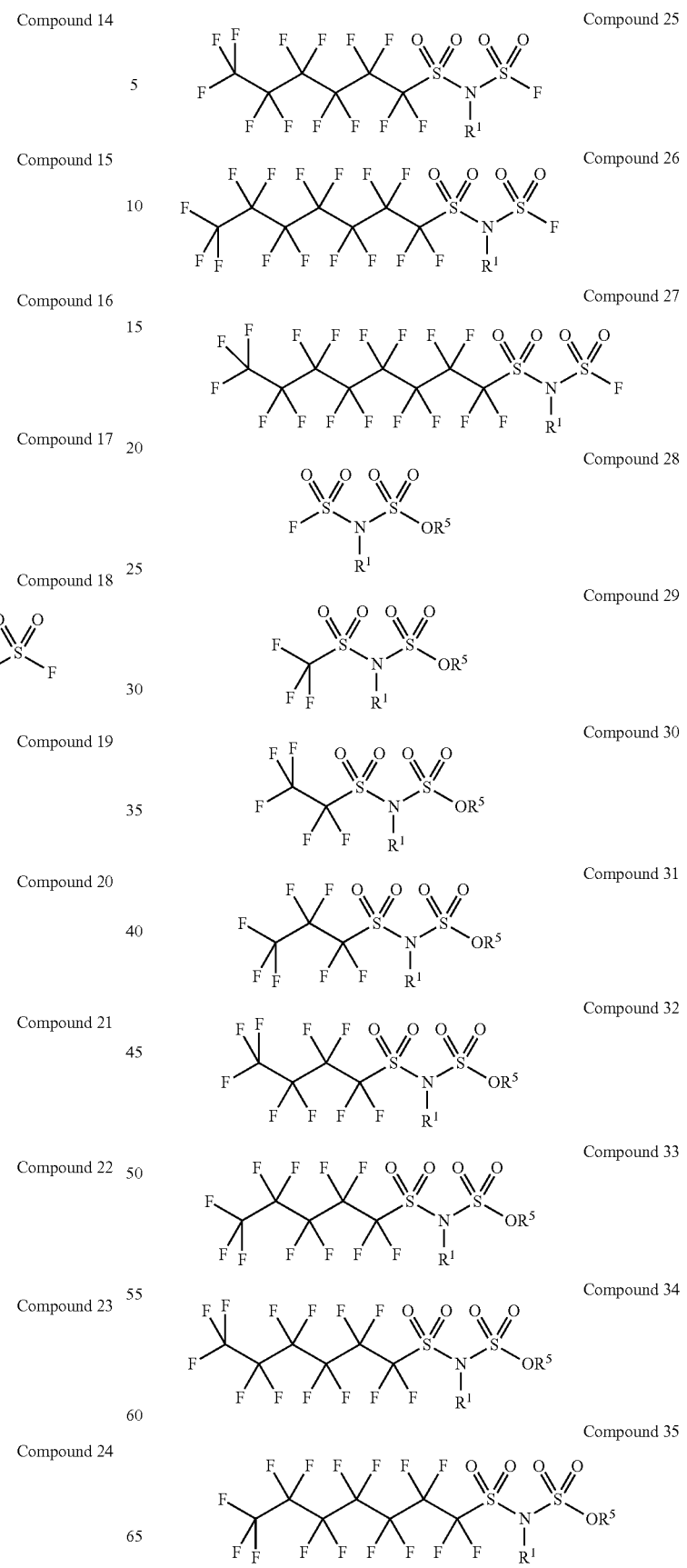

Compound 36

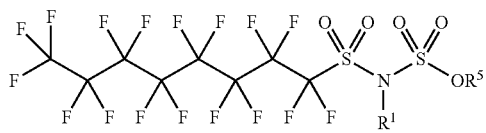

wherein $R^1$ is as previously defined and $R^5$ is an optionally halogenated linear or branched $C_1$-$C_{24}$alkyl group, or $OR^5$ is $O^-(M^{n+})_{1/n}$ or $O^-X^+$, wherein M, X and n are as herein defined.

Also described are processes for the preparation of sulfamic acid derivatives as defined in the present document. Examples to such processes are illustrated in Scheme 1:

ents (i.e. having no hydrogen atom covalently bound to the nitrogen atom). Examples of tertiary amines include, without limitation, the following amines: trimethylamine, triethylamine, tripropylamine, tributylamine, diisopropylethylamine, N-alkyl substituted pyrrolidines and morpholines, quinuclidine, N-methylimidazole, pyridine, picoline, lutidine, quinoline, N,N-dimethylaniline, and other similar amines. For instance, the sulfur trioxide source and tertiary amine are used in the form of a sulfur trioxide-tertiary amine complex.

Chlorinating agents which may be used for the conversion of substituted sulfamic acid and tertiary amine salts into substituted sulfamoyl chlorides can be selected from inorganic and organic acid chlorides, for example, $PCl_5$, $POCl_3$, $SOCl_2$, $ClSO_3H$, $COCl_2$, $ClCOCOCl$, sulfur chlorides, cyanuric chloride, acetyl chloride, trifluoroacetyl chloride,

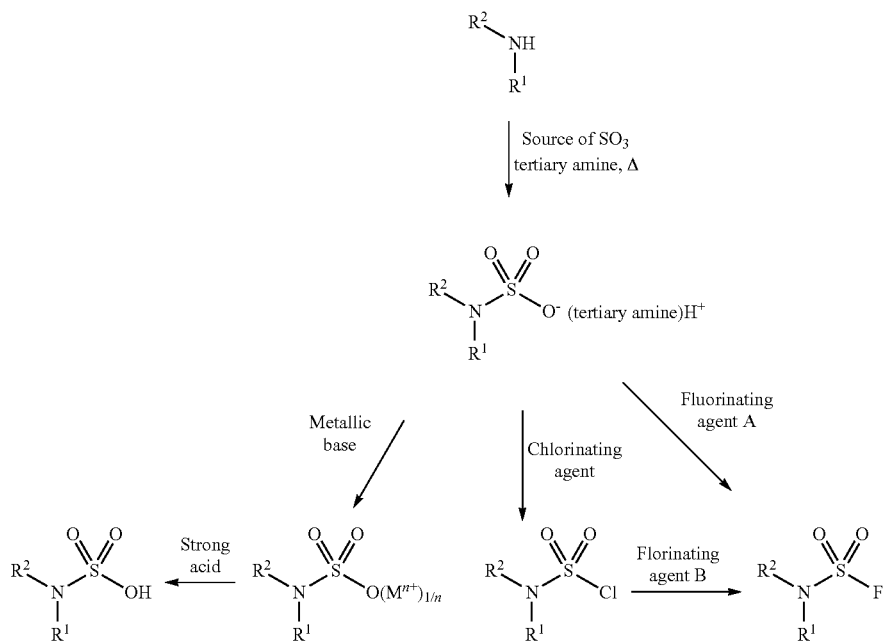

Scheme 1 wherein $R^1$, $R^2$, M and n are as previously defined.

Sources of $SO_3$ include any chemical compound which can generate sulfur trioxide under specific reaction conditions. For instance, these compounds may be selected from the following reagents: $SO_3$ (sulfur trioxide itself) and its oligomers and polymers; $H_2SO_4$ (sulfuric acid); $H_2S_2O_7$ (disulfuric acid) and other polysulfuric acids and their salts; $ClSO_3H$ (chlorosulfonic acid) and its salts; $FSO_3H$ (fluorosulfonic acid) and its salts; $SO_3$-ammonia complex (sulfamic acid); complexes of sulfur trioxide with organic amines such as trimethylamine, triethylamine, tripropylamine, tributylamine, diisopropylethylamine, N-alkyl substituted pyrrolidines and morpholines, pyridine, picoline, lutidine, quinoline, N,N-dimethylaniline, and other amines; complexes of sulfur trioxide with other organic compounds like dioxane, thioxane, dimethylformamide; and acylsulfates which are generated by introduction of $SO_3$ into dry carboxylic acids (without water), for example, acetyl sulfate ($CH_3C(O)OSO_3H$).

Tertiary amines used in the reactions illustrated in the above Scheme 1 are amines having three organic substitumethanesulfonyl chloride, trifluoromethanesulfonyl chloride, benzoyl chloride, (trichloromethyl)benzene, benzenesulfonyl chloride, toluenesulfonyl chloride and other compounds known to a person skilled in the art. In some chlorination examples, it may be advantageous to add small amounts of N,N-dimethylformamide or other N,N-disubstituted carboxamides as catalyst.

Fluorinating agents A which may be used for the direct transformation of substituted sulfamic acid and tertiary amine salts into substituted sulfamoyl fluorides can be selected from reactive inorganic and organic acid fluorides, for example, $PF_5$, $POF_3$, $SOF_2$, $FSO_3H$, $COF_2$, $FCOCOF$, organic and inorganic hexafluorophosphates, hexafluorosilicates, tetrafluoroborates, sulfur tetrafluoride and its organic derivatives like DAST (diethylaminosulfur trifluoride) and morpholinosulfur trifluoride; cyanuric fluoride, acetyl fluoride, (trifluoromethyl)nezene, trifluoroacetyl fluoride, methanesulfonyl fluoride, trifluoromethanesulfonyl fluoride, benzoyl fluoride, benzenesulfonyl fluoride, toluenesulfonyl fluoride and other compounds which can be selected by a person skilled in the art.

Fluorinating agents B which can be used for the transformation of substituted sulfamoyl chlorides into substituted sulfamoyl fluorides include less reactive fluorinating agents such as hydrogen fluoride and fluoride salts, for instance, ammonium, sodium, potassium, and cesium fluorides and their hydrogen difluoride equivalents (example $HN_4^+HF_2^-$). Complex salts of amines and hydrofluoric acid, like pyridinium and triethylammonium polyhydrofluorides. Additionally, all fluorinating agents A listed in the preceding paragraph may also be used as fluorinating agents B.

The metallic base includes any basic compound containing at least one cation of a metal as counter ion of a basic anion. Known examples include metal hydroxides, alkoxides and, in special cases, substituted metal amides, but organometallics and Grignard reagents could also be used as particularly strong bases.

Examples of strong acids suitable for the coversion of substituted sulfamic acid salts into free sulfamic acids must have a pKa lower than that of the substituted sulfamic acid or should form an insoluble precipitate with said metallic cation. Examples of such acids comprise hydrochloric acid, hydrobromic acid, sulfuric acid, nitric acid, and trifluoromethanesulfonic acid. An acidic ion exchange resin could also be used as strong acid source.

The processes for preparing sulfamic acid derivatives defined herein comprise a first step which is the sulfonation of an amine or amide with sulfur trioxide or one of its reactive derivatives in the presence of a tertiary amine. The product thus obtained is the second compound in the above Scheme 1, for instance, a compound of Formula I as herein defined, in which $R^3$ is $O^-X^+$, where $X^+$ represents a protonated tertiary amine, i.e. the compound of Formula I is a tertiary ammonium salt of a substituted sulfamic acid (e.g. a tertiary ammonium salt of a substituted amidosulfonate). This sulfonation step, which results in the formation of a sulfamoyl group, is very fast, having a significant advantage over the existing processes described above.

After this first sulfonation step, additional steps may be carried out to obtain the various compounds defined by Formula I. These additional steps will depend on the desired final product.

A first category is the transformation of the amidosulfonate group into a sulfamoyl chloride group. In this case, the substituted sulfamic acid tertiary ammonium salt obtained in the first step is reacted with a chlorinating agent to substitute the oxygen atom with a chlorine atom. Similarly, the conversion of the amidosulfonate group into a sulfamoyl fluoride group will be achieved by reacting the substituted sulfamic acid tertiary ammonium salt with a strong fluorinating agent, thereby replacing the oxygen atom by a fluorine atom, or the sulfamoyl chloride group, obtained by chlorination, may be converted into a sulfamoyl fluoride group using milder fluorinating agents.

If a metallic salt of a divalent sulfamic acid (such as a substituted azanidosulfonate), with a negative charge on both the nitrogen atom and on the sulfonate oxygen atom (see Formula I where $R^1$ is $(M^{n+})_{1/n}$ and $R^3$ is $O^-(M^{n+})_{1/n}$), is desired, the substituted sulfamic acid tertiary ammonium salt obtained in the first step is reacted with a metallic base in order to substitute the tertiary ammonium cation with a metallic cation. Those salts can also be used to prepare a free substituted sulfamic acid by reacting metallic salts with a strong acid or by the contacting a solution of a substituted sulfamic acid salt with an acidic ion exchange resin.

Starting compounds for the preparation of sulfamic acid derivatives are selected from substituted amines, and simple or substituted amides. For example, primary alkylamines may allow to obtain N-substituted sulfamic acid derivatives, for instance, N-alkylimidodisulfuric acid salts and other derivatives of N-alkylimidodisulfuric acid, primary carboxamides and primary sulfamides may make it possible to obtain mixed secondary amides, and N-alkylamides may afford mixed N-alkylated secondary amides.

In the first step, a substituted amine or amide (carboxamide or sulfonamide) compound, possessing at least one hydrogen atom on the nitrogen atom (which can be sulfonated), is placed in a reactor, and a tertiary amine is then added. The obtained mixture may be optionally diluted in an appropriate unreactive solvent (e.g. DMF, dioxane, dichloroethane and others). The obtained mixture may also be reacted without solvent addition. The tertiary amine may be selected from commercially available products, for example, trimethylamine, triethylamine, tripropylamine, tributylamine, N-alkyl substituted pyrrolidines and morpholines, N-methylimidazole, pyridine, picoline, lutidine, quinoline, N,N-dimethylaniline, diisopropylethylamine, quinuclidine, and others. Then, the sulfonating agent is slowly added to the reaction mixture while monitoring the temperature since in some cases the reaction may be exothermic. For example, the sulfonating agent is selected from $SO_3$ (sulfur trioxide itself) and its oligomers and polymers; $H_2SO_4$ (sulfuric acid); $H_2S_2O_7$ (disulfuric acid) and other polysulfuric acids and their salts; $ClSO_3H$ (chlorosulfonic acid) and its salts; $FSO_3H$ (fluorosulfonic acid) and its salts; $SO_3$-ammonia complex (sulfamic acid); complexes of sulfur trioxide with organic amines such as trimethylamine, triethylamine, tripropylamine, tributylamine, diisopropylethylamine, N-alkyl substituted pyrrolidines and morpholines, picoline, lutidine, quinoline, N,N-dimethylaniline, and other amines; complexes of sulfur trioxide with other organic compounds such as dioxane, thioxane, dimethylformamide; and acylsulfates generated by introduction of $SO_3$ into dry carboxylic acids (i.e. in absence of water), for example, introducing $SO_3$ in anhydrous acetic acid affords acetyl sulfate ($CH_3C(O)OSO_3H$). After addition of all reagents, the mixture is stirred at a temperature between room temperature and 300° C., preferably between 50° C. and 250° C. Once the reaction is completed, the product is, in most cases, obtained in a solid form ready for further use or in crystalline form, separated by filtration, and optionally purified by recrystallization.

According to an example, in the first step of the process, the substituted amine or amide is mixed in solid state with a sulfur trioxide and tertiary amine solid complex, preferably the sulfur trioxide is a pyridine-sulfur trioxide, trimethylamine-sulfur trioxide or triethylamine-sulfur trioxide complex, which are commercially available. The molar ratio between amide and sulfur trioxide complex in the mixture is preferably around 1:1, i.e. 1 for each sulfonyl group to be introduced in the molecule. The so obtained mixture is stirred and heated under inert atmosphere at a temperature within the range of from 50° C. and 300° C., preferably within the range of from 100° C. to 250° C., in order to melt the reaction mixture and allow the reaction to proceed. The reaction time is short, usually ending in less than 10 h, or less than 4 h, or even less than 1 h. After cooling, the substituted amidosulfonate tertiary ammonium salt crystallises from the melt. The compound may also be recrystallized from an organic solvent but may be used as such in the following steps.

The tertiary ammonium amidosulfonate may be further converted to a sulfamoyl chloride group by reaction with a chlorinating agent selected from inorganic and organic acid chlorides, for example, $PCl_5$, $POCl_3$, $SOCl_2$, $ClSO_3H$, $COCl_2$, ClCOCOCl, sulfur chlorides, cyanuric chloride, acetyl chloride, trifluoroacetyl chloride, methanesulfonyl chloride, trifluoromethanesulfonyl chloride, benzoyl chloride, (trichloromethyl)benzene, benzenesulfonyl chloride, toluenesulfonyl chloride and other compounds known to a person skilled in the art. In some cases, it may be advantageous to add small amounts of dimethylformamide or other N,N-disubstituted carboxamides as catalyst. Chlorinating agent selection depends on the compounds used in the process and must be adjusted to each specific derivative of sulfamic acid but, in most cases, thionyl chloride ($SOCl_2$) may be used as reagent. The molar ratio between the tertiary ammonium amidosulfonate and the chlorinating agent is set so that, for each mole of amidosulfonate group, at least 1 mole of active chloride is used, but an excess is often used to accelerate the reaction and ensure its completion.

To perform the conversion, the appropriate chlorinating agent and tertiary ammonium amidosulfonate are mixed neat or diluted with an appropriate unreactive solvent, for example dichloroethane, and the mixture is heated to a temperature within the range of from 30° C. to 300° C., preferably within the range from 40° C. to 200° C., and more particularly to the mixture's reflux temperature. Reaction time is generally short, usually completing in less than 24 h, less than 12 h, or even less than 4 h. After completion, the produced sulfamoyl chloride can be extracted from the reaction mixture using a low polarity organic solvent.

For instance, the second step of the process may be achieved by treating the reaction mixture from the preceding steps, without further purification, with a chlorinating agent, preferably $PCl_5$, $POCl_3$, $SOCl_2$, $ClSO_3H$, $COCl_2$, ClCOCOCl, more particularly $SOCl_2$, $COCl_2$, ClCOCOCl which form gaseous by-products and thus enable easier isolation of the desired product. The reaction mixture from the first step may also be pulverized in order to increase the reaction rate. Rate may also be accelerated by the addition of about 5 mol % of DMF or other N,N-disubstituted carboxamides as catalyst. The mixture is stirred and heated under inert atmosphere at a temperature between 50° C. and 300° C., preferably at a temperature between 100° C. and 250° C. in order to melt the reaction mixture and allow the reaction to proceed. Reaction time is generally short and the reaction is typically completed in less than 24 h, less than 12 h, or even less than 4 h. During the process, a complex mixture of tertiary amine hydrochloride, of chlorinating agent by-products, and of substituted sulfamic acid chloride (sulfamoyl chloride compound), is obtained. To purify the substituted sulfamic acid chloride, the mixture is extracted with a solvent that dissolves the desired product and does not dissolve the tertiary amine salts. After extraction, the substituted sulfamic acid chloride may be distilled or crystalized to afford the product as a pure or essentially pure compound. If this step is an intermediate step in the preparation of sulfamoyl fluoride compounds, the extract could also be used in a fluorination step without any further purification.

The transformation of tertiary ammonium amidosulfonates to sulfamoyl fluorides may be achieved, inter alia, in two possible ways, either by direct fluorination of the tertiary ammonium salt or by fluorination of the sulfamoyl chloride group obtained by the step described in the preceding paragraphs.

Direct fluorination of tertiary ammonium amidosulfonate is carried out by reacting the starting material with a strong fluorinating agent, which can be selected from reactive inorganic and organic acid fluorides including $PF_5$, $POF_3$, $SOF_2$, $FSO_3H$, $COF_2$, FCOCOF, organic and inorganic hexafluorophosphates, hexafluorosilicates, tetrafluoroborates, sulfur tetrafluoride and its organic derivatives (such as diethylaminosulfur trifluoride (DAST) and morpholinosulfur trifluoride), cyanuric fluoride, acetyl fluoride, trifluoroacetyl fluoride, methanesulfonyl fluoride, trifluoromethanesulfonyl fluoride, benzoyl fluoride, (trifluoromethyl)benzene, benzenesulfonyl fluoride, toluenesulfonyl fluoride and other similar compounds known in the field. Selection of the fluorinating agent depends on the compounds used in the process and must be adjusted to each specific sulfamic acid derivative. The molar ratio between the tertiary ammonium amidosulfonate and the fluorinating agent is set so that, for each mole of amidosulfonate group, at least 1 mole of active fluoride is used, but an excess may also be used to accelerate the reaction and/or ensure its completion.

To perform this conversion, the appropriate fluorinating agent and the tertiary ammonium amidosulfonate are mixed neat or diluted with an appropriate unreactive solvent, for example dichloroethane. The mixture is then heated at a temperature within the range of from 30° C. to 300° C., preferably within the range from 40° C. to 200° C., and more particularly to the mixture's reflux temperature. The reaction time is short, generally being complete in less than 24 h, less than 12 h, or even less than 4 h. After reaction, the sulfamoyl fluoride may be extracted from the reaction mixture with a low polarity organic solvent.

For instance, for a direct fluorination, the reaction mixture from the first step (e.g. without further purification) may be mixed with a fluorinating agent, such as sulfur tetrafluoride or one of its organic derivatives (like DAST (diethylaminosulfur trifluoride) or morpholinosulfur trifluoride), cyanuric fluoride, acetyl fluoride, trifluoroacetyl fluoride, methanesulfonyl fluoride, trifluoromethanesulfonyl fluoride, benzoyl fluoride, (trifluoromethyl)benzene, benzenesulfonyl fluoride, and toluenesulfonyl fluoride, which are liquid and form less toxic by-products, enabling easier isolation of the desired product. The reaction mixture from the previous step may also be pulverized prior to its use in the present step in order to increase the reaction rate. The mixture is stirred under inert atmosphere at a temperature within the range of 50° C. to 300° C., preferably within the range of 100° C. to 250° C., in order to melt the mixture and allow the reaction to proceed. The reaction time is short since it is typically complete in less than 24 h, less than 12 h, or even less than 4 h. During this process, a complex mixture of tertiary amine hydrofluoride, of fluorinating agent by-products and of the desired substituted sulfamic acid fluoride (sulfamoyl fluoride compound), is obtained. To purify the substituted sulfamic acid fluoride, the mixture may be extracted with a solvent in which the desired product is soluble and that does not dissolve or dissolves very little of most of the impurities. After extraction, the substituted sulfamic acid fluoride can also be further distilled or crystalized to afford the product in pure or essentially pure form.

On the other hand, indirect fluorination is achieved by reacting a sulfamoyl chloride compound with a reactive fluorinating agent, which may be selected from reactive inorganic and organic fluorides, for example, $PF_5$, $POF_3$, $SOF_2$, $FSO_3H$, $COF_2$, FCOCOF, organic and inorganic hexafluorophosphates, hexafluorosilicates, tetrafluoroborates, sulfur tetrafluoride and its organic derivatives (like DAST or morpholinosulfur trifluoride), cyanuric fluoride, acetyl fluoride, trifluoroacetyl fluoride, methanesulfonyl fluoride, trifluoromethanesulfonyl fluoride, benzoyl fluoride, benzenesulfonyl fluoride, toluenesulfonyl fluoride, hydrogen fluoride and fluoride salts (e.g. ammonium, sodium, potassium, or cesium fluoride or hydrogen difluoride salts), and a complex salt of amine and hydrofluoric acid (such as pyridinium or triethylammonium polyhydrofluoride), and other compounds known to a person skilled in the art. The selection of a fluorinating agent depends on the compounds used in the process and is adapted to each sulfamic acid specific derivative to be produced. The molar ratio between the sulfamoyl chloride group and the fluorinating agent used is set so that, for each sulfamoyl chloride group, at least 1 mole of active fluoride is used, but an excess is preferably used to accelerate the reaction and/or ensure its completion.

The conversion may be carried out by mixing the appropriate fluorinating agent and sulfamoyl chloride compound neat or diluted in an appropriate unreactive solvent, for example, dichloromethane, dichloroethane, toluene or their combinations, and by heating the mixture at a temperature within the range of 30° C. to 300° C., preferably within the range of 40° C. to 200° C., and more particularly at the mixture's reflux temperature. In some cases, the reaction is very exothermic so it should be carefully monitored and the fluorinating agent be added slowly to the chloride or vice versa. The reaction time is generally short and typically ends in less than 24 h, less than 12 h, or less than 4 h. After completion, the produced sulfamoyl fluoride can be extracted from the reaction mixture using a low polarity organic solvent.

For instance, a sulfamoyl chloride compound, extracted from the chlorination step may be mixed, without further purification, with a fluorinating agent, for example, with hydrogen fluoride or a fluoride salt (e.g. ammonium, sodium, potassium, or cesium fluoride or hydrogen difluoride salt), and a complex salt of amine and hydrofluoric acid (such as pyridinium or triethylammonium polyhydrofluorides), which are easier to obtain and have economical advantages over other fluorinating agents. The mixture is then stirred under inert atmosphere at a temperature within the range of 30° C. to 300° C., preferably between 30° C. and 150° C., in order to melt the reaction mixture and allow the reaction to proceed. Reaction time is generally short and the reaction typically ends in less than 24 h, less than 12 h, or less than 4 h. During the process, a complex mixture of by-products, formed of the fluorinating agent and of the desired substituted sulfamic acid fluoride compound is obtained. To purify the substituted sulfamic acid fluoride, the mixture may be extracted with a solvent in which the desired product is soluble, and that does not dissolve or dissolves very little of most of the impurities. After extraction, the substituted sulfamic acid fluoride may be further purified by distillation or crystallization to afford the product in pure or essentially pure form.

If salts of divalent sulfamic acids (such as substituted azanidosulfonate), having a negative charge on the nitrogen atom and on the sulfonate oxygen atom, are contemplated, primary amines or amides should be used as starting material in the sulfonation step. The sulfonation step then provides the tertiary amine N-monosubstituted sulfamate. These compounds can be easily transformed into metallic salts by treatment with a suitable metallic base. Examples of metallic bases which can be considered for carrying out this conversion are relatively strong bases, including alkaline and alkaline earth metal hydroxides, alkoxides, and substituted amides, organometallics and Grignard reagents.

To perform this conversion, the appropriate metallic base (at least 2 equivalents, e.g. about 2,2 equivalents thereof vs. amidosulfonate) and the tertiary ammonium amidosulfonate are mixed and diluted in an appropriate unreactive solvent, for example water and/or an aliphatic lower alcohol (such as alcohols having from 1 to 4 carbon atoms), and the mixture is heated at a temperature within the range of 30° C. to 300° C., or within the range of 40° C. to 200° C., or at the mixture's reflux temperature. The reaction time is quite short, typically being complete in less than 24 h, less than 12 h, or less than 4 h. After completion and cooling of the reaction mixture, the product (i.e. an azanidosulfonate) may directly crystalize out of the solution, or the mixture may be concentrated, and the solid residue be recrystallized in an appropriate solvent.

For instance, the reaction mixture (from the first step, without purification) is added to a solution of at least 2 equivalents of alkaline or alkaline earth base, such as LiOH, NaOH, KOH, RbOH, CsOH, Be(OH)$_2$, Mg(OH)$_2$, Ca(OH)$_2$, Sr(OH)$_2$, Ba(OH)$_2$, or alkoxides of Li, Na, K, Rb, Cs, Be, Mg, Ca, Sr, or Ba. The solvent used for this reaction is selected from water and lower alcohols like methanol, ethanol, isopropanol, propanol, and butanol, or one of their combinations. It is preferable to use a minimum amount of solvent to dissolve the reaction materials. The mixture is then stirred under inert atmosphere at a temperature within the range of 50° C. to 300° C., or within the range of 100° C. to 250° C. The reaction generally proceeds quickly and may typically be complete in less than 24 h, less than 12 h, or even less than 4 h. During the process, a complex mixture of free tertiary amine, sulfonating agent by-products and desired substituted azanidosulfonate of the metal is obtained. In some cases, the reaction product crystalizes out of the mixture upon cooling. In other cases, the mixture is concentrated to remove volatile compounds and the product is extracted with a solvent and/or recrystallized to afford the product in pure or essentially pure form. These salts may be used to prepare free substituted sulfamic acids by reacting the metallic salts with a strong acid or by contacting the salt solution and an acidic ion exchange resin. These free substituted sulfamic acids may also be used as starting materials for the preparation of other salts which could not be obtained directly through neutralization with corresponding bases.

In some cases, the desired salts of substituted sulfamic acids can be prepared by cation metathesis, i.e. a cationic exchange in an ionic reaction driven by the formation and precipitation of an insoluble compound. For example, lithium bis(fluorosulfonyl)imide could be prepared from lithium perchlorate and potassium bis(fluorosulfonyl)imide in acetonitrile. When mixing a solution of both reagents, the insoluble potassium perchlorate precipitates while lithium bis(fluorosulfonyl)amide remains into solution.

The sulfamic acid derivatives described herein can, in some embodiments, be used as electrolytes or in electrolyte compositions of electrochemical cells like batteries, electrochromic devices and capacitors. Such electrochemical cells comprise an anode, a cathode, and an electrolyte. For example, the sulfamic acid derivatives are in liquid state at the operation temperature of the electrical appliance they are destined to. They can themselves be liquid or can be solubilized in a solvent suitable for use in electrolytes. It may be possible to prepare such electrolytes from the sulfamic acid derivatives only or from their mixture with other compounds.

In one embodiment, the compounds for the preparation of electrolytes may be represented by Formula II or III:

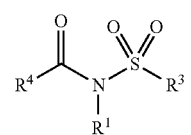

Formula II

-continued

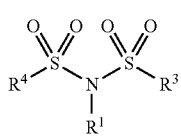

Formula III wherein $R^1$, $R^3$, and $R^4$ are as previously defined. For instance, $R^1$ is selected from Li, Na, K, Rb, Cs, Be, Mg, Ca, Sr, Ba, and Al; $R^3$ is selected from F and Cl; and $R^4$ is selected from fluorine, chlorine, the optionally halogenated linear or branched $C_1$-$C_{24}$alkyl, $C_6$-$C_{10}$aryl or $C_5$-$C_{10}$heteroaryl groups, for instance, a perfluorinated linear or branched $C_1$-$C_{24}$alkyl, a perfluorinated $C_6$-$C_{10}$aryl, or a perfluorinated $C_5$-$C_{10}$heteroaryl.

In another embodiment, the compounds for the preparation of electrolytes may be represented by Formula IIa or IIIa:

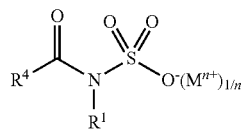

Formula IIa

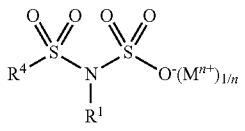

Formula IIIa wherein $R^1$, $R^4$, M and n are as previously defined, for instance, $R^1$ is $(M^{n+})_{1/n}$ and M in each instance is selected from Li, Na, K, Cs, Rb, Be, Mg, Ca, Sr, Ba, and Al and n is an integer selected from 1 to 3.

In one embodiment, the electrolytes are prepared from these sulfamic acid derivatives by dissolution in an appropriate electrolyte solvent or a solvating polymer for polymer electrolyte preparation. For use in lithium and lithium ion batteries, lithium salts of sulfamic acid derivatives may be dissolved at an appropriate concentration, for example between 0.05 and 3 mol/litre. For other types of batteries, other salts of sulfamic acid derivatives should be dissolved, for example, sodium salts for sodium batteries, magnesium salts for magnesium batteries, and the like.

Non-limiting examples of electrolyte solvents include dimethyl carbonate, diethyl carbonate, ethyl methyl carbonate, propylene carbonate, ethylene carbonate, γ-butyrolactone, glyme, diglyme, triglyme, tetraglyme, sulfolane, tetraethylsulfamide, and combinations thereof. Various additives may also be added in the electrolyte composition to improve its properties.

Non-limiting examples of polymers include poly(ethylene oxide) and its copolymers and block copolymers, poly(propylene oxide) and its copolymers and block copolymers, poly(dimethylsiloxane) and its copolymers and block copolymers, poly(alkylene carbonate) and its copolymers and block copolymers, poly(alkylenesulfone) and its copolymers and block copolymers, poly(alkylenesulfamide) and its copolymers and block copolymers, polyurethanes and their copolymers and block-copolymers, poly(vinylalcohol) and its copolymers and block copolymers, and combinations thereof. Additionally, branched or crosslinked solvating polymers may also be included.

Various additives may also be included in the polymer electrolyte composition to improve its properties. For instance, (unsaturated) carbonates, like vinylene carbonate, fluoroethylene carbonate and fluorovinylene carbonate, and ethane derivatives (i.e. vinylic compounds) can be added to improve stability at high and/or low voltage, for example at a concentration of from about 0.1 to about 15 percent by weight, based on the total weight of the electrolyte.

In another embodiment, the sulfamic acid derivatives may also be used as alkylating agents, for example, the compounds of Formulae II and III above, wherein:

$R^1$ is selected from optionally perhalogenated linear or branched $C_1$-$C_{24}$alkyl, aryl and heteroaryl groups;

$R^3$ is F or Cl; and $R^4$ is selected from a fluorine or chlorine atom, and the linear or branched $C_1$-$C_{24}$alkyl, $C_6$-$C_{10}$aryl, $C_5$-$C_{10}$heteroaryl, perfluorinated linear $C_1$-$C_{24}$alkyl, perfluorinated $C_6$-$C_{10}$aryl, and perfluorinated $C_5$-$C_{10}$heteroaryl groups.

Those compounds may react with organic bases such as amines, phosphines, and sulfides to form N-, P-, and S-alkylated compounds respectively. In some cases, when tertiary amines and tertiary phosphines are used in the reaction, ionic liquids may be obtained directly with hydrophobic anions, these being normally accessible only through elaborate alkylations with haloalkanes followed by anionic metathesis in a solvent using an alkali metal salt with a hydrophobic anion.

EXAMPLES

The following non-limiting examples are for illustrative purposes only and should not be construed as further limiting the scope of the present technology as contemplated.

Example 1: Preparation of ammonium imidodisulfonate

This procedure illustrates the rapid sulfonation ability of an ammonia-sulfur trioxide complex (sulfamic acid).

Finely powdered sulfamic acid (9.7094 g, 0.1 mol) was mixed with powdered ammonium sulfamate (11.412 g, 0.1 mol) in a 100 mL round bottom flask equipped with a condenser and a magnetic stirring bar, and brought under dry argon. The mixture was heated and stirred in an oil bath at 150° C. The mixture melted and resolidified to a crystalline mass within a few minutes. The mixture was then cooled down and IR analysis gave a spectrum identical to that of an authentic sample.

IR [KBr]/cm$^{-1}$: Very broad 3228(vs), 3145(sh), 1403(vs), 1263(vs), 1225(vs), 1086(m), 1027(s), 867 (s), 598(s), 535 (m), 460(w).

Example 2: Preparation of potassium imidodisulfonate

The following step b) illustrates the rapid sulfonation achieved with the trimethylamine-sulfur trioxide complex, while step c) illustrates the reaction of a trialkyalmmonium sulfamate with a metallic base to prepare a metallic sulfamate.

a) Trimethylammonium sulfamate

Sulfamic acid (19.418 g, 0.2 mol) was dissolved in 30 mL of a 45% trimethylamine aqueous solution and the mixture was left standing to slowly evaporate. The title compound crystallised as colourless crystals, which were filtered off and dried in an oven at 90° C., IR analysis showed absence of crystallisation water and confirmed the structure, the characteristic peaks for sulfamate and trimethylammonium ions being observed.

IR [KBr]/cm$^{-1}$: 3318(s), 3269(m), 2955(m), 2700(s), 2475(s), 1546(w), 1476(m), 1427(w), 1222(vs), 1128(m), 1059(s), 985(s), 809(s), 588(s), 562(s).

b) Trimethylammonium imidodisulfonate

Trimethylammonium sulfamate (3.12 g, 20 mmol) and trimethylamine-sulfur trioxide complex (2.78 g, 20 mmol) were mixed in a tube with a heat gun until a clear melt was obtained (5 min, approximately 200° C.). After cooling, the mass resolidified as a glassy solid. Characteristic peaks for the imidodisulfonate anion and trimethylammonium cation were present in the solid's IR spectrum.

IR [KBr]/cm$^{-1}$: 3231(m), 2956(m), 2703(s), 2475(m), 1477(m), 1427(w), 1384(m), 1259(vs), 1219(vs), 1087(m), 1032(s), 985(s), 879(m), 600(m), 535(w).

c) Potassium imidodisulfonate

The glassy solid obtained in b) was dissolved in 15 mL of water containing potassium hydroxide (3.4 g, 60 mmol) and the mixture was heated to reflux for 10 min. No precipitate formed during this step, which indicated that no or very small amounts of $K_2SO_4$ (insoluble in these conditions) was formed, the observation being indicative of a quantitative reaction in step (b). The reaction mixture was then cooled in an ice/water bath and neutralized to pH=7 to obtain a precipitate in the form of colourless needles. The product's IR spectrum was identical to that of a potassium imidodisulfonate authentic sample.

IR [KBr]/cm$^{-1}$: 3228(s), 1384(m), 1265(vs), 1242(vs), 1228(vs), 1088(m), 1029(s), 985(s), 875(m), 600(s), 537(s).

Example 3: Preparation of pyridinium N-trifluoromethanesulfonylsulfamate

This procedure illustrates the fast and high yield sulfonation of trifluoromethanesulfonylamide (triflamide) by the pyridine-sulfur trioxide complex.

Triflamide (1.49 g, 10 mmol) and pyridine-sulfur trioxide complex (1.75 g, 11 mmol) were weighted in a 25 mL round bottom flask equipped with a condenser and brought under dry argon. The mixture was heated using a heat gun until a clear yellowish melted product was obtained (approx. 180° C.). The flask was stirred (swirled) by hand to ensure good mixing. After 5 min, the mixture was cooled down and a glassy solid was first obtained, which crystallised in about 1 h. $^{9}$F NMR analysis of the sample showed that the triflamide was transformed into the title compound with a nearly quantitative yield.

$^1$H NMR (300 MHz, DMSO-d$_6$) δ/ppm: 8.10 (t, J=7.11 Hz, 2H), 8.55-8.67 (m, 1H), 8.94 (d, J=5.31 Hz, 2H), 13.71 (br. s., 2H);

$^{13}$C NMR (75 MHz, DMSO-d$_6$) δ/ppm: 120.17 (q, J=324.00 Hz), 127.34 (s), 142.32 (s), 146.40 (s); and $^{19}$F NMR (282 MHz, DMSO-d$_6$) δ/ppm: -78.14 (s).

Example 4: Preparation of trimethylammonium N-trifluoromethanesulfonylsulfamate

This procedure illustrates the rapid and high yield sulfonation of triflamide using the trimethylamine-sulfur trioxide complex.

Triflamide (1.49 g, 10 mmol) and trimethylamine-sulfur trioxide complex (1.39 g, 10 mmol) were weighted in a 25 mL round bottom flask equipped with a condenser and brought under dry argon. The mixture was heated using a heat gun until a clear yellowish melted product was obtained (about 180° C.). The flask was stirred (swirled) by hand to ensure good mixing. After 5 min, the mixture was cooled down and the product immediately crystallised. NMR analysis of the sample showed that the vast majority of the triflamide was transformed into the title compound, i.e. with a yield of about 97%, as observed by $^{19}$F NMR.

$^1$H NMR (300 MHz, DMSO-d$_6$) δ/ppm: 2.78 (s, 9H), 9.37 (br. s, 2H);

$^{13}$0 NMR (75 MHz, DMSO-d$_6$) δ/ppm: 44.27 (s), 120.19, (q, J=324.00 Hz);

$^{19}$F NMR (282 MHz, DMSO-d$_6$) δ/ppm: -78.14 (s).

Example 5: Preparation of N-(fluorosulfonyl)trifluoromethanesulfonylamide (FTFSI)

This procedure illustrates the fast and high yield transformation of a substituted sulfamic salt into a substituted sulfamoyl fluoride compound.

To a cooled reaction mixture, freshly prepared according to Example 3, was added $SOCl_2$ (5 mL) and the mixture was stirred and refluxed for 1 h to form the chlorosulfamoyltriflamide intermediate. Thionyl chloride excess was then evaporated. Dichloromethane (5 mL) and potassium fluoride (3 g) were added and the obtained mixture was heated under reflux for 30 min. The reaction mixture was then cooled down, carefully dissolved in cold water and basified with potassium hydroxide. Tetrabutylammonium chloride (1 g) was added and the mixture was extracted with dichloromethane (3×10 mL). The organic layers were then combined and concentrated. NMR analysis showed that the extract contained tetrabutylammonium N-(fluorosulfonyl)trifluoromethanesulfonimide.

$^1$H NMR (300 MHz, DMSO-d$_6$) δ/ppm: 0.92 (t, J=7.24 Hz, 3H), 1.31 (sxt, J=7.38 Hz, 2H), 1.46-1.71 (m, 2H), 3.02-3.29 (m, 2H); and $^{19}$F NMR (282 MHz, DMSO-d$_6$) δ/ppm: -78.03 (d, J=3.88 Hz, 3 F), 57.37 (q, J=3.90 Hz, 1 F)).

Example 6: Preparation of N-fluorosulfonyl-nonafluorobutanesulfonylamide

Step b) of this process illustrates the fast and high yield transformation of a substituted sulfamide into a substituted sulfamoyl fluoride compound.

a) Nonafluorobutanesulfonylamide

Liquid ammonia (120 mL) was condensed in a 500 mL Schlenk-type round bottom flask equipped with a magnetic stirrer. At -50° C., nonafluorobutanesulfonyl fluoride (84 g, 284 mmol) was added dropwise under stirring over a period of one hour to the partly frozen ammonia. The mixture was then allowed to warm up to room temperature, and afterwards stirred overnight. The flask's content was washed with cold water into a beaker, acidified with hydrochloric acid to a pH<1 and extracted with ethyl acetate (4×50 mL). The organic layers were combined, dried with $Na_2SO_4$ and concentrated to afford 80 g (95%) of a colourless oil which solidified as a white waxy solid upon standing.

$^1$H NMR (303 MHz, acetone-d$_6$) δ/ppm: 8.15 (br. s, 1H);

$^{13}$C NMR/$^{19}$F decoupled (76 MHz, acetone-d$_6$) δ/ppm: 109.71 (s), 111.59 (s), 114.71 (s), 118.34 (s); and $^{19}$F NMR (285 MHz, acetone-d$_6$) δ/ppm: -125.31--124.84 (m, 2 F), -120.66--119.92 (m, 2 F), -113.03--112.74 (m, 2 F), -80.13 (tt, J=10.04, 2.45 Hz, 3 F).

b) N-fluorosulfonyl-nonafluorobutanesulfonylamide

Nonafluorobutanesulfonylamide (3.19 g, 10.7 mmol) from step (a) and the pyridine-sulfur trioxide complex (1.95 g, 12.3 mmol) were weighted into a 25 mL round bottom flask equipped with a condenser and brought under dry argon. The mixture was heated using a heat gun until a clear yellowish melted product was obtained (about 180° C.). The flask was stirred (swirled) by hand to ensure good mixing. After 15 min, the mixture was cooled down and a glassy solid formed. To this cooled mixture, $SOCl_2$ (5 mL) was added and the mixture was stirred under reflux during 1 h to form the chlorosulfamoylamide intermediate. Excess thionyl chloride was evaporated, $CH_2Cl_2$ (5 mL) and potassium fluoride (3 g) were added and the mixture was heated under reflux for 30 min. The mixture was then cooled down, carefully dissolved in cold water and basified (with KOH). Tetrabutylammonium chloride (1 g) was added and the mixture was extracted with $CH_2Cl_2$ (3×10 mL). The organic layers were combined and concentrated. $^{19}F$ NMR analysis showed a characteristic triplet of triplets at +58 ppm, which could be assigned to the fluorosulfamoyl group attached to nonafluorobutanesulfonylamide (coupled with two $CF_2$ groups), which would confirm the presence of N-fluorosulfonyl-nonafluorobutanesulfonylamide.

$^{19}F$ NMR (285 MHz, acetone-$d_6$) δ/ppm: −124.96--−124.82 (m, 2 F), −120.06--−119.91 (m, 2 F), −111.50--−111.32 (m, 2 F), −80.23--−80.18 (m, 3 F), 58.05 (tt, J=5.10, 1.30 Hz, 1 F).

Example 7: Preparation of N-fluorosulfonyltridecafluorohexanesulfonylamide a) Tridecafluorohexanesulfonylamide Liquid ammonia (30 mL) was condensed in a 100 mL Schlenk-type round bottom flask equipped with a magnetic stirrer. At −50° C., tridecafluorohexanesulfonyl fluoride (25 g, 62 mmol) is added dropwise, while stirring, over a period of one hour to the partly frozen ammonia. The mixture was then allowed to warm up to room temperature, and then stirred overnight. The flask's content was washed with cold water into a beaker, acidified with HCl until a pH<1 and extracted with ethyl acetate (4×50 mL). The organic layers were combined, dried with $Na_2SO_4$ and concentrated to afford 18 g (73%) of a waxy solid.

$^1H$ NMR (303 MHz, acetone-$d_6$) δ/ppm: 8.15 (br. s, 1H);
$^{19}F$ NMR (285 MHz, acetone-$d_6$) δ/ppm: −126.97--−126.62 (m, 2 F), −123.34 (br. m., 2 F), −122.43 (br. m., 2 F), −121.09--−120.66 (m, 2 F), −114.51--−114.24 (m, 2 F), −81.81--−81.67 (m, 3 F).

b) Pyridinium N-tridecafluorohexanesulfonylsulfamate

Tridécafluorobutanesulfonylamide (1 g, 2.5 mmol) from step (a) and the pyridine-sulfur trioxide complex (0.62 g, 3.9 mmol) were weighted into a 25 mL round bottom flask equipped with a condenser and brought under dry argon. The mixture was heated using a heat gun until a clear yellowish melted product was obtained (about 180° C.). The flask was stirred (swirled) by hand to ensure good mixing. After 15 min, the mixture was cooled down and a glassy solid formed. NMR analysis confirmed that all pyridine was in the form of pyridinium ion and that sulfonation had occurred on the amide group, as indicated by the shift of the two $CF_2$ groups closest to the sulfonyl group.

$^1H$ NMR (303 MHz, DMSO-$d_6$) δ/ppm: 7.95-8.17 (m, 2H), 8.59 (s, 1H), 8.93 (d, J=4.89 Hz, 2H) 11.52-12.99 (br.s, 2H);

$^{19}F$ NMR (285 MHz, DMSO-$d_6$) δ/ppm: −125.80 (br. s., 2 F), −122.55 (br. s., 2 F), −121.68 (br. s., 2 F), −120.46--−119.94 (m, 2 F), −111.53 (br.t, J=14.50 Hz, 2 F), −80.58--−80.01 (m, 3 F).

Tetrabutylammonium N-fluorosulfonyltridecafluorohexanesulfonimide $SOCl_2$ (5 mL) was added to the cooled mixture of step (b), which was stirred under reflux for 6 h to form the chlorosulfamoylamide intermediate. Excess thionyl chloride was evaporated, $CH_2Cl_2$ (5 mL) and $KHF_2$ (3 g) were added and the mixture was heated under reflux for 30 min. The reaction mixture was then cooled down, carefully dissolved in cold water and basified (with $NaHCO_3$). Tetrabutylammonium chloride (1 g) was added and the mixture was extracted with $CH_2Cl_2$ (3×10 mL). The organic layers were combined and concentrated. $^{19}F$ NMR analysis showed a characteristic triplet of triplets at +58 ppm, which was assigned to the fluorosulfamoyl group attached to the tridecafluorohexanesulfonimide group (coupled with two $CF_2$ groups, also confirmed by $^{19}F$-gCOSY experiment), which demonstrated the presence of tetrabutylammonium N-fluorosulfonyltridecafluorohexanesulfonimide in the extract.

$^1H$ NMR (303 MHz, CDCl$_3$) δ/ppm: 0.92-1.07 (m, 3H), 1.45 (sxt, J=7.34 Hz, 2H), 1.57-1.78 (m, 2H), 3.19-3.39 (m, 2H);

$^{19}F$ NMR (285 MHz, CDCl$_3$) δ/ppm: −126.59--−125.92 (m, 2 F), −122.85 (br. s., 2 F), −121.89 (br. s., 2 F), −120.38 (br. s, 2 F), −112.66--−112.28 (m, 2 F), −80.87 (tt, J=9.93, 2.34 Hz, 3 F), 57.81 (tt, J=5.35, 1.30 Hz, 1 F).

Example 8: Preparation of dipotassium N-tosyl-azanidesulfonate

Tosylamide (3.42 g, 20 mmol) and the pyridine-sulfur trioxide complex (3.66 g, 23 mmol) were weighted into a 25 mL round bottom flask equipped with a condenser and brought under dry argon. The mixture was heated using a heat gun until a clear yellowish melt was obtained (about 200° C.). The flask was stirred (swirled) by hand to ensure good mixing. After 10 min, the mixture was allowed to cool down and a crystalline solid formed. A 2 g quantity of this solid was dissolved in cold water (40 mL) and KOH was added to bring the pH to 10. Acetic acid was then added to set the pH at 7.4. This solution was poured in isopropanol (150 mL) and put in the refrigerator overnight. A precipitate formed and was filtered, washed with cold isopropanol and recrystallized from a water/isopropanol mixture to afford 1.62 g of dipotassium N-tosylazanidesulfonate.

$^1H$ NMR (303 MHz, D$_2$O) δ/ppm: 2.41 (s, 3H), 7.37 (d, J=8.51 Hz, 2H), 7.76 (d, J=8.08 Hz, 2H);
$^{13}C$ NMR (76 MHz, D$_2$O) δ/ppm: 22.15 (s), 127.90 (s), 130.68 (s), 142.28 (s), 143.77 (s).

Example 9: Preparation of N-ethyl-bis(fluorosulfonyl)imide

Pyridinium N-ethylsulfamate (2.04 g, 10 mmol) and the pyridine-sulfur trioxide complex (1.75 g, 11 mmol) were weighted into a 25 mL round bottom flask equipped with a condenser and brought under dry argon. The mixture was heated using a heat gun until a clear yellowish melted product was formed (about 180° C.). The flask was stirred (swirled) by hand to ensure good mixing. After 5 min, the mixture was cooled down to obtain a first glassy solid which crystallised in 1 h. To this cooled mixture, POCl$_3$ (5 mL) was added and the mixture was stirred and heated under reflux for 6 h to form the chlorosulfamoylamide intermediate.

Excess phosphoryl chloride was evaporated, $CH_2Cl_2$ (5 mL) and $KHF_2$ (3 g) were added and the mixture was heated under reflux for 30 min. The reaction mixture was then cooled down, carefully dissolved in cold water and extracted with $CH_2Cl_2$ (2×10 mL). The organic layers were combined and concentrated. NMR spectroscopy analysis revealed the presence of N-ethyl-(bisfluorosulfonyl)imide in the extract, since the characteristic couplings between fluorine and the ethyl group protons were observed.

$^1H$ NMR (303 MHz, $CDCl_3$) δ/ppm: 1.48 (tt, J=7.20, 0.60 Hz, 3H), 4.10 (qt, J=7.09, 1.70 Hz, 2H);

$^{13}C$ NMR (76 MHz, $CDCl_3$) δ/ppm: 14.21 (br. s), 51.56 (br. s);

$^{19}F$ NMR (285 MHz, $CDCl_3$) δ/ppm: 59.08-59.12 (m).

Example 10: Preparation of Potassium N-(fluorosulfonyl)trifluoromethanesulfonimide (KTFSI)

Triflamide (14.9 g, 100 mmol) and the pyridine-sulfur trioxide complex (19.2 g, 120 mmol) were weighted in a 100 mL round bottom flask equipped with a condenser and a magnetic stirring bar, and brought under dry argon. The mixture was stirred and heated in an oil bath (180° C.) until a clear yellowish melt was obtained (20-25 min). The mixture was then cooled to 70° C., thionyl chloride (10 mL, 140 mmol) was added through the condenser and gas evolution was monitored using a bubbler. After gas evolution ceased (about 3.5 h), the mixture was cooled down to room temperature, dissolved in a toluene and $CH_2Cl_2$ mixture, added to flame dried potassium fluoride (35 g) and heated under reflux for 1 h. The mixture was then cooled, the solvent was evaporated under vacuum and the residue was extracted with butyl acetate and THF. The combined extracts were concentrated under vacuum and the product was precipitated by the addition of dichloromethane to afford 17.3 g (nearly 80%) of KTFSI.

IR [KBr]/cm$^{-1}$: 1375(m), 1356(vs), 1323(s), 1206(vs), 1183(s), 1160(vs), 1080(s), 850(m), 778(m), 744(w), 635(s), 605(m), 575(m), 532 (w).

$^{13}C$ NMR (126 MHz, acetone-$d_6$) δ/ppm: 125.34 (dq, J=321.40, 2.30 Hz,);

$^{19}F$ NMR (285 MHz, acetone-$d_6$) δ/ppm: −77.53 (d, J=3.90 Hz, 3 F), 57.53 (q, J=4.20 Hz, 1 F).

Example 11: Preparation of lithium bis(fluorosulfonyl)imide by anion Exchange Dry KFSI (10.96 g, 50 mmol) and $LiClO_4$ (5.32 g) salts were weighted in a 250 mL round bottom flask in a glovebox. Under argon and with vigorous stirring, 100 mL of dry acetonitrile were added via cannula. The salts dissolved immediately, a white precipitate formed a few moments later, and the mixture heated spontaneously up to approximately 40° C. The mixture was then stirred overnight, and a $KClO_4$ precipitate was filtered off. The filtrate was concentrated under reduced pressure and the resulting oily product was dried under high vacuum at 60° C. to afford 11.80 g (nearly quantitative yield) of LiFSI as a white solid. The $^{19}F$ NMR spectrum was practically identical to that obtained for KFSI.

Example 12: Preparation of lithium N-(fluorosulfonyl)trifluoromethansulfonimide by anion Exchange Dry KTFSI (13.462 g, 50 mmol) and $LiI_4$ (5.32 g) salts were weighted in a 250 mL round bottom flask in a glovebox. Under argon and with vigorous stirring, 100 mL of dry acetonitrile were added using a cannula. The salts dissolved immediately, a white precipitate formed a few moments later, and the mixture warmed up spontaneously to approximately 35° C. The mixture was then stirred overnight, and a $KClO_4$ precipitate was removed by filtration. The solvent was evaporated under vacuum and the resulting oil was dried under high vacuum at 80° C. to obtain 11.80 g (nearly quantitative yield) of LiFTFSI as a white solid. $^{13}C$ and $^{19}F$ NMR spectra were practically identical to those obtained for KTFSI.

Example 13: Use of lithium bis(fluorosulfonyl)imide as electrolyte in Li-ion Batteries Cell Preparation:

Lithium bis(fluorosulfonyl)imide (LiFSI) prepared as in Example 11 was dissolved in a 3:7 (vol:vol) mixture of ethylene carbonate (EC) and diethyl carbonate (DEC) to obtain an electrolyte having a 1 M salt concentration.

To perform an electrochemical test with an active insertion cathode, a $LiFePO_4$ (LFP) electrode was prepared using a mixture of $LiFePO_4$, carbon black and poly(vinylidene fluoride) (PVDF) in a ratio of 84:3:3:10 (% by weight) in N-methylpyrrolidone (NMP). This mixture was then coated on an aluminum current collector. The electrode material was dried at 120° C. in a vacuum oven for 12 h before use.

To perform an electrochemical test with an active insertion anode, a graphite (OMAC, Osaka Japan) electrode was prepared by mixing graphite, carbon black and PVDF in a ratio of 92:2:6 (% by weight) in NMP, which was then coated on a copper current collector. The electrode material was dried at 120° C. in a vacuum oven for 12 h before use.

After drying, the electrodes were cut (by punch) to a size fitting a coin-type cell assembly. The above-mentioned electrolyte was used in these coin-type cells using the graphite or LFP electrode, a polypropylene separator and metallic lithium as electrode of opposing polarity.

Tests on Cells:

The cells comprising graphite were cycled between 2.5 and 0.01 V vs. Li metal and the cells containing LFP between 2.0 and 4.0 V vs. Li metal. Formation of the coin cells was carried out at a rate C/24 (see FIGS. 1(a) and (b)).

For LFP, a capacity of 155 mAh/g at the 1$^{st}$ cycle and a coulombic efficiency of 97.3% were obtained and, in the 2$^{nd}$ cycle, a capacity of 158 mAh/g and a coulombic efficiency of over 99% were obtained. These good results confirm that the salt prepared by the present process qualifies for use in LFP-containing electrochemical cells.

For graphite, a capacity of 355 mAh/g at the 1$^{st}$ cycle and a coulombic efficiency of 91.6% were reached, indicating an SEI (solid electrolyte interface) layer formation and, at the 2$^{nd}$ cycle, a capacity of 362 mAh/g with a coulombic efficiency of 99% were obtained. These very good results confirm that the salt produced by the present process also qualifies for use with graphite in electrochemical cells.

Figure 2:
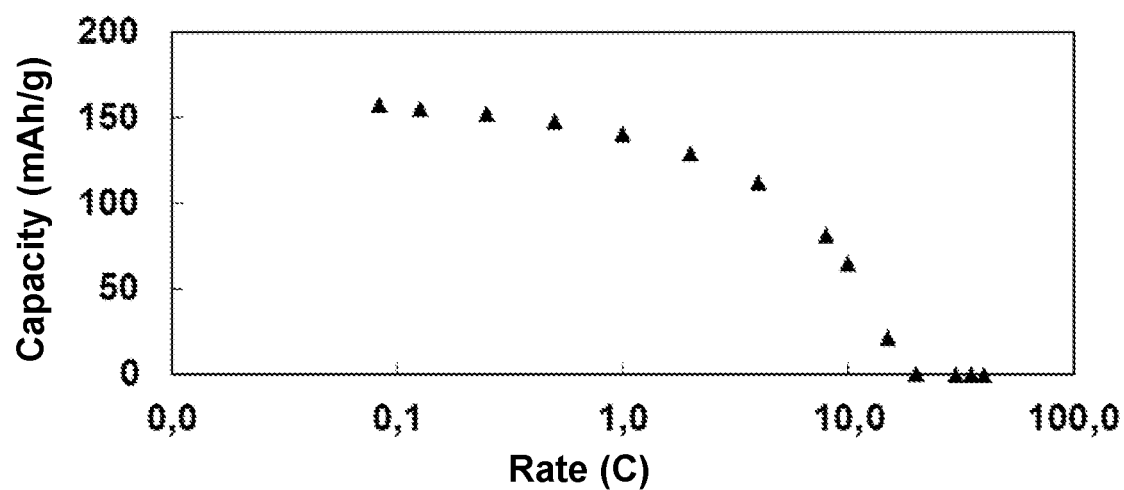
FIG. 2 shows the discharge capacity as a function of discharge rate (power capability) for a cell or half-cell using an electrolyte containing LiFSI produced by the present process respectively with (a) LiFePO$_4$ and (b) graphite as electrode material, according to Example 13.
Figure 2:
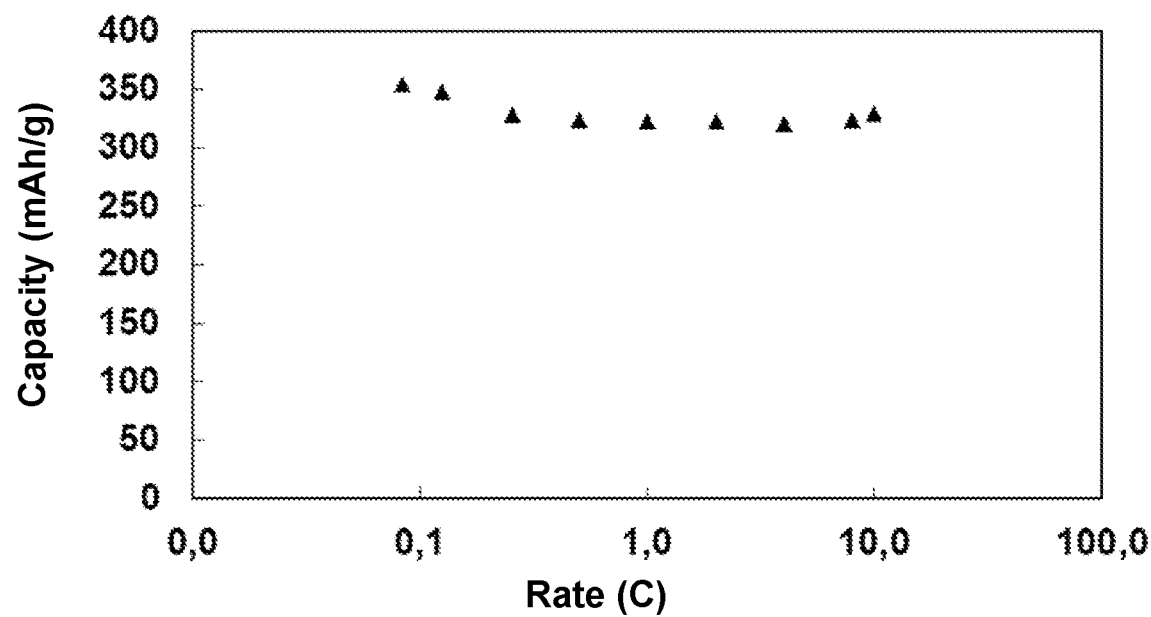

These same cells were tested for their rate capability by measuring the variations in discharge capacity as a function of the discharge rate (results shown in FIGS. 2(a) and (b)). For LFP, an expected drop in capacity was observed at high rates. To the opposite, with graphite, a retention of capacity over 300 mAh/g was observed even for a 10 C rate, demonstrating that the SEI layer formed on graphite with the LiFSI electrolyte is of very good quality.

Figure 3:
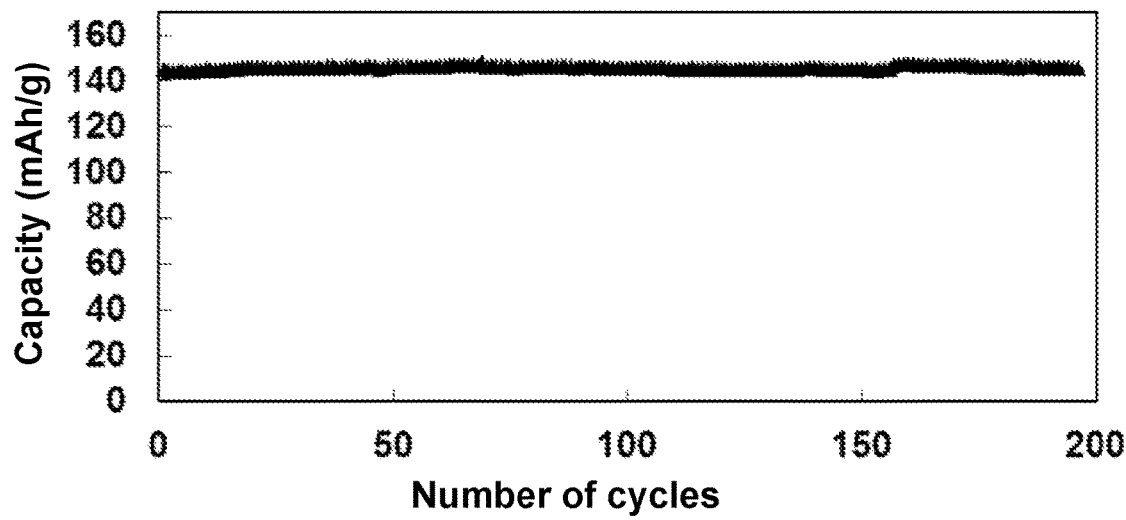
FIG. 3 shows stability test results, illustrated as the variation in cell capacity as a function of the number of cycles, for a cell or half-cell using an electrolyte containing LiFSI produced by the present process respectively with (a) LiFePO$_4$ and (b) graphite as electrode material, according to Example 13.
Figure 3:
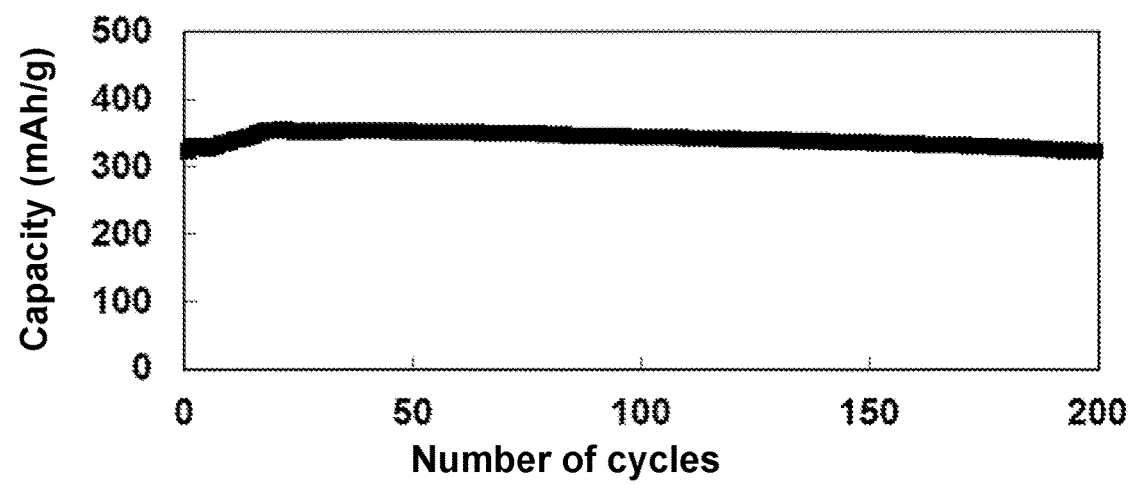

The cells were also submitted to stability testings using a charge rate C/4 and a discharge rate 1 C (results presented in FIGS. 3(a) and (b)). Cells comprising LFP showed excellent capacity retention with 146 mAh/g in the 195th cycle. With graphite, an expected slight fading of capacity was observed, however, the capacity still being of 322 mAh/g after 200 cycles.

The above results confirm that LiFSi produced by the present process is suitable for use as electrolyte salt in lithium or lithium-ion batteries.

Example 14: Use of lithium N-(fluorosulfonyl)trifluoromethansulfonimide as electrolyte in Li-ion Batteries Lithium N-(fluorosulfonyl)trifluoromethansulfonimide (LiFTFSI) prepared as in Example 12 was dissolved in a 3:7 (vol:vol) mixture of ethylene carbonate (EC) and diethyl carbonate (DEC) to obtain a 1 M concentration electrolyte.

Figure 4:
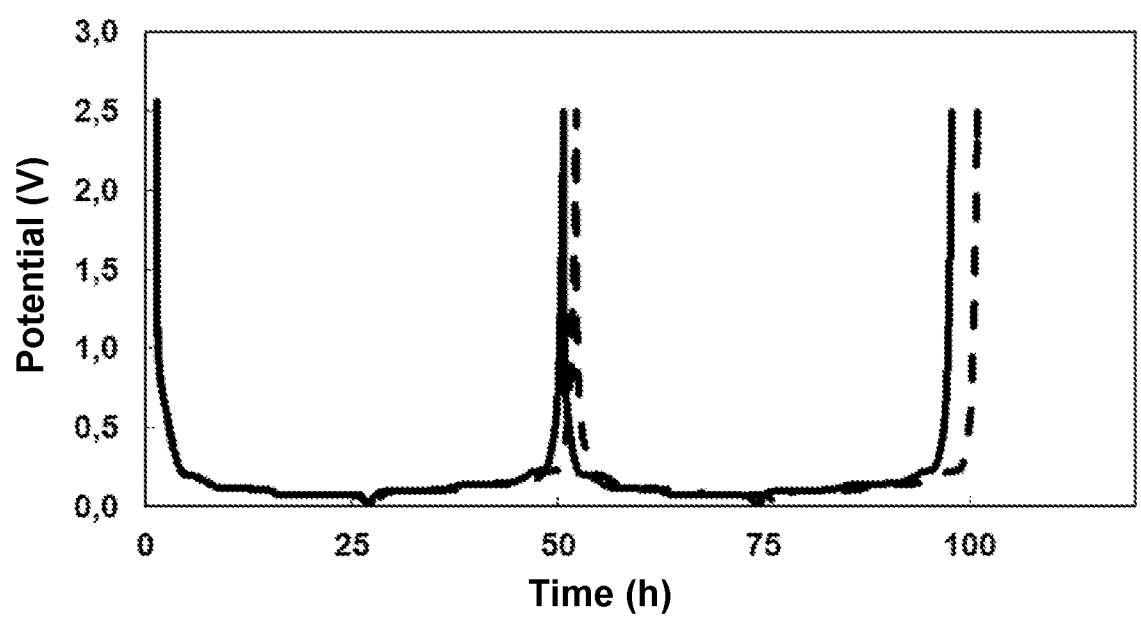
FIG. 4 presents the potential as a function of time at the formation step in two identical half-cells using an electrolyte containing LiFTFSI produced by the present process with a graphite electrode according to Example 14.

To perform electrochemical tests with an active insertion anode, a graphite (OMAC, Osaka Japan) electrode was prepared as in Example 13. The electrolyte was used in coin-type cells using the graphite electrode, a polypropylene separator and metallic lithium as electrode of opposing polarity. The cell was cycled between 2.5 and 0.01 V vs. Li metal. Formation of the coin cell was done at a rate C/24 (results presented in FIG. 4).

A capacity of 363 mAh/g for the 1st cycle and a coulombic efficiency of 90% were reached, indicating the formation of a SEI layer and, in the 2nd cycle, a capacity of 363 mAh/g with a coulombic efficiency of 98.7% were obtained. These very good results confirm that the salt prepared according to the present process qualifies for use with graphite in electrochemical cells.

Figure 5:
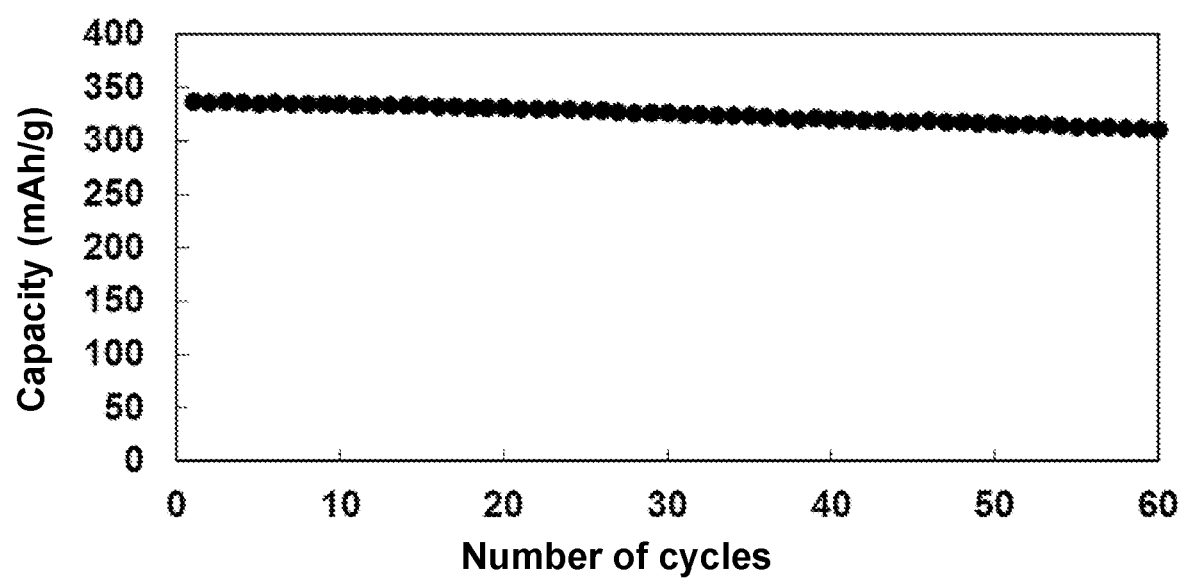
FIG. 5 shows results of stability tests, illustrated as the variation in cell capacity as a function of the number of cycles, for a half-cell using an electrolyte containing LiFT-FSI produced by the present process with a graphite electrode according to Example 14.

The cells were also subjected to stability tests with a charge rate C/4 and a discharge rate 10 C (results for graphite presented in FIG. 5). As expected, the cell containing graphite exhibited a slight fading of capacity, but the capacity still reached 310 mAh/g in the 60th cycle.

Example 15: Comparison of Rate Capability for LiPF$_6$, LiFSI and LiFTFSI used with a graphite electrode 1 M LiPF$_6$, LiFSI and LiFTFSI solutions were prepared by dissolving the salts in a 3:7 (vol/vol) mixture of ethylene carbonate (EC) and diethyl carbonate (DEC). The LiPF$_6$ solution also contained 2% by weight of vinylene carbonate.

Figure 6:
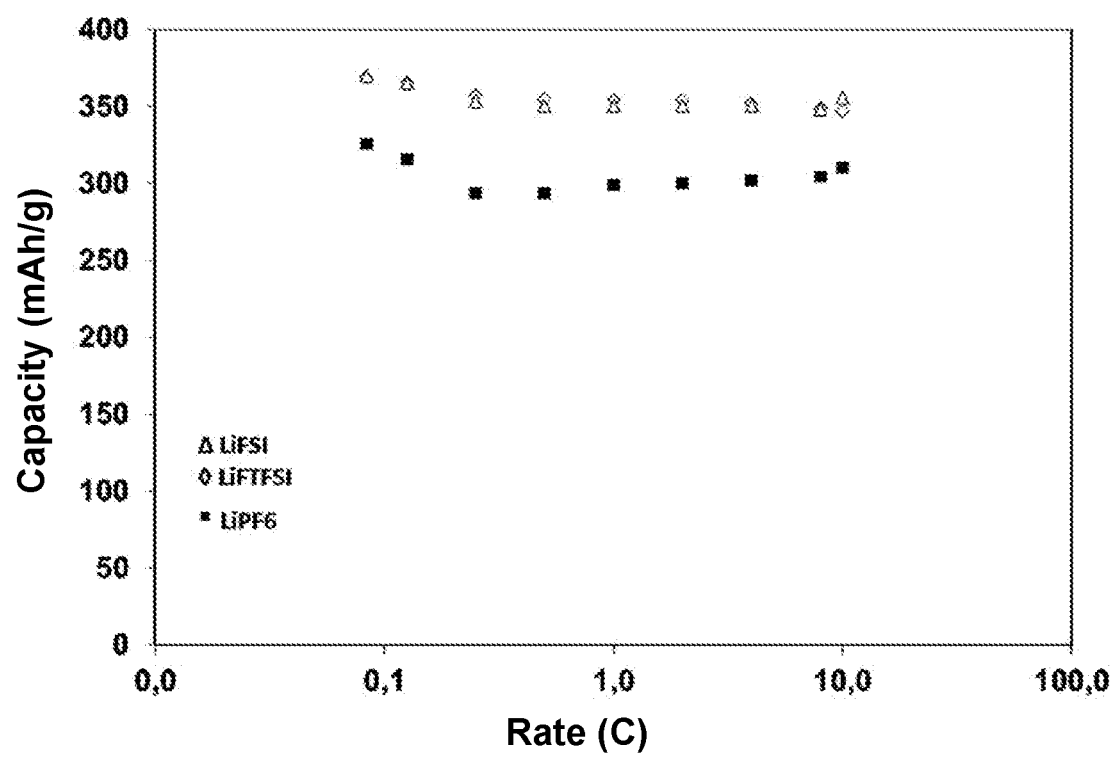
FIG. 6 shows comparative discharge capacity data as a function of discharge rate (power capability) for 3 half-cells using an electrolyte containing LiFSI (triangles), LiFTFSI (lozenges), both being produced by the present process, and LiPF$_6$ (squares) with a graphite electrode according to Example 15.

Coin-type cells were prepared using metallic lithium and graphite electrodes as described in Example 13, a polypropylene separator, and the above solutions as electrolytes. The cells were cycled between 2.5 and 0.01 V vs. Li metal. All cells were submitted to two formation cycles at C/24 and then rate capability was examined by measuring discharge capacity as a function of the discharge rate (see FIG. 6).

LiFSI and LiFTFSI salts exhibited nearly-identical characteristics with respect to power capability, which was approximately 50 mAh/g higher than that of LiPF$_6$ over all power ranges. This indicates that the SEI layer formed on graphite with both the LiFSI and LiFTFSI electrolytes is of superior quality to the one formed when LiPF$_6$ is used. The two salts prepared according to the present process are thus very suitable for use in electrolytes of lithium or lithium-ion batteries, for instance, using a graphite anode.

Numerous modifications could be made to any one of the above-described embodiments without departing from the scope of the present invention. References, patents or scientific literature documents referred to in this application are incorporated herein by reference in their entirety and for all purposes.

The invention claimed is:

1. A process for the preparation of a sulfamic acid derivative of Formula I:

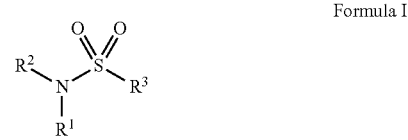

Formula I wherein,
R$^1$ is selected from the group consisting of a hydrogen atom and linear or branched C$_1$-C$_{24}$alkyl, C$_6$-C$_{10}$aryl and C$_5$-C$_{10}$heteroaryl groups, said groups being optionally halogenated, or R$^1$ and the adjacent nitrogen atom together form a salt wherein the nitrogen atom is negatively charged (anion) and R$^1$ is (M$^{n+}$)$_{1/n}$ or X$^+$;

R$^2$ is selected from the group consisting of perfluorinated linear or branched C$_1$-C$_{24}$alkanoyl, perfluorinated C$_6$-C$_{10}$aryloyl, perfluorinated C$_5$-C$_{10}$heteroaryloyl, perfluorinated linear or branched C$_1$-C$_{24}$alkanesulfonyl, perfluorinated C$_6$-C$_{10}$arylsulfonyl, and perfluorinated C$_5$-C$_{10}$heteroarylsulfonyl;

R$^3$ is F;

(M$^{n+}$) is a metal cation, wherein M is a metal and n is an integer selected from the range of 1 to 4; and X$^+$ represents an organic cation;

the process comprising the steps of:

i) contacting a compound of the formula:

with a complex of sulfur trioxide and of a tertiary amine and heating at a temperature comprised between about 50° C. and about 300° C.

ii) optionally contacting the product of step (i) with a chlorinating agent; and iii) contacting the product obtained in step (i), or in step (ii) when present, with a fluorinating agent to produce a compound of Formula I.

2. The process of claim 1, wherein the tertiary amine is selected from trimethylamine, triethylamine, tripropylamine, tributylamine, diisopropylethylamine, N-alkyl substituted pyrrolidines and morpholines, pyridine, picoline, lutidine, quinoline, and N,N-dimethylaniline.

3. The process of claim 1, wherein step (i) is carried out without addition of solvent.

4. The process of claim 1, the process comprising step (ii).

5. The process of claim 4, wherein the fluorinating agent in step (iii) is selected from hydrogen fluoride, fluoride or hydrogen difluoride salts, and a complex salt of amines and hydrofluoric acid.

6. The process of claim 1, wherein step (ii) is absent and said fluorinating agent in step (iii) is selected from reactive inorganic and organic acid fluorides.

7. The process according to claim 1, wherein the sulfamic acid derivative is defined according to Formula II or III:

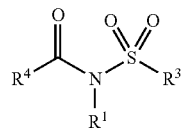
Formula II

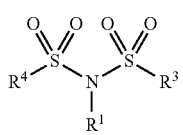
Formula III wherein, $R^1$ and $R^3$ are as defined in claim 1;

$R^4$ is selected from the group consisting of a linear or branched $C_1$-$C_{24}$alkyl, a $C_6$-$C_{10}$aryl or a $C_5$-$C_{10}$heteroaryl, each being perfluorinated.

8. The process according to claim 7, wherein $R^4$ is a perfluorinated linear or branched $C_1$-$C_{24}$alkyl.

9. The process according to claim 1, wherein $R^1$ is $(M^{n+})_{1/n}$ and M is selected from Li, Na, K, Rb, Cs, Be, Mg, Ca, Sr, Ba, Al, Zn, Cu, Sc, Y, Fe, Co, Ni, Ti, Sn, V, Cr, and Mn.

10. The process according to claim 1, wherein $R^1$ is selected from linear or branched $C_1$-$C_{24}$alkyl, $C_6$-$C_{10}$aryl and $C_5$-$C_{10}$heteroaryl, each being optionally perhalogenated.

11. The process according to claim 1, wherein the sulfamic acid derivative is selected from the following Compounds 10 to 27:

Compound 10
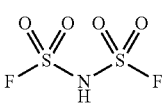

Compound 11
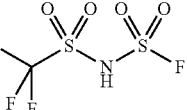

Compound 12
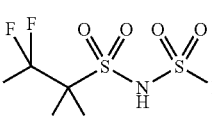

Compound 13
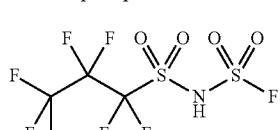

Compound 14
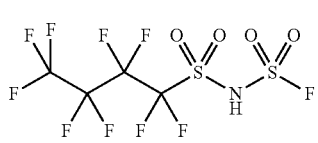

Compound 15
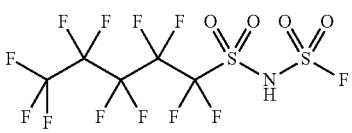

Compound 16
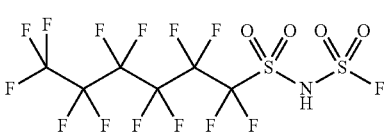

Compound 17
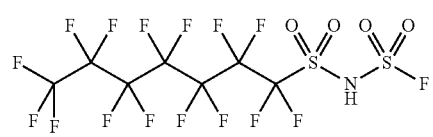

Compound 18
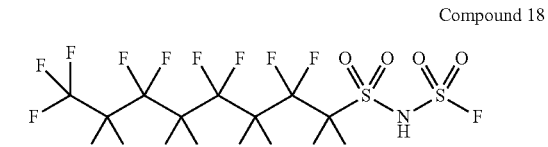

Compound 19
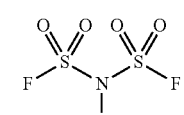

Compound 20
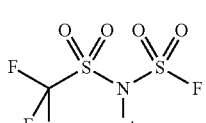

Compound 21
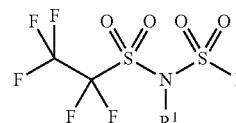

Compound 22
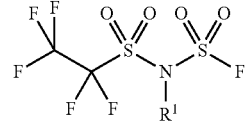

Compound 23
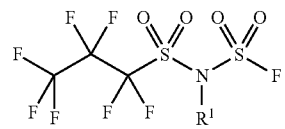

Compound 24
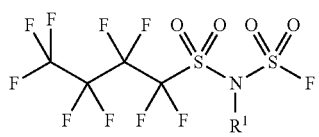

Compound 25
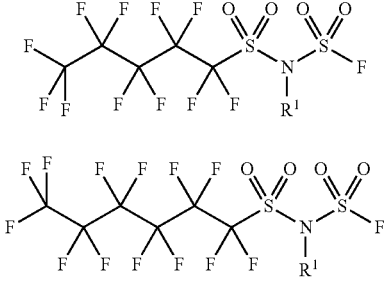

-continued

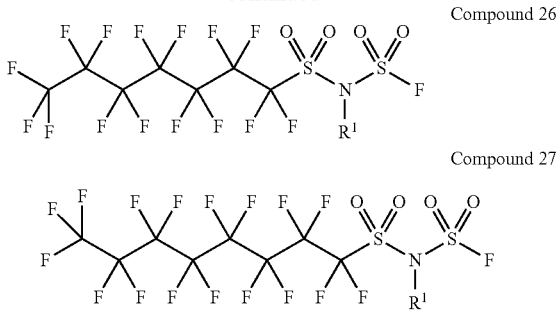

Compound 26

Compound 27 wherein R¹ is as defined in claim 1.

12. The process of claim 1, wherein M is selected from Li, Na, K, Rb, Cs, Be, Mg, Ca, Sr, Ba, Al, Zn, Cu, Sc, Y, Fe, Co, Ni, Ti, Sn, V, Cr, and Mn.

13. The process of claim 1, wherein M is selected from Li, Na, K, Rb, Cs, Be, Mg, Ca, Sr, Ba, Al, Zn, Sc, and Ti.

14. The process of claim 1, wherein M is an alkali metal, alkaline earth metal, or aluminum.

15. The process of claim 1, wherein M is selected from Li, Na, K, Rb, Cs, Be, Mg, Ca, Sr, and Ba, and n is 1 or 2.

16. The process of claim 1, wherein X⁺ is selected from ammonium, alkylammonium, dialkylammonium, trialkylammonium, tetraalkylammonium, 1,3-dialkylimidazolium, N-alkylpyrrolidinium, N-alkylpiperidinium, trialkyloxonium, trialkylsulfonium, and tetraalkylphosphonium.

17. The process of claim 1, wherein step (i) comprises heating at a temperature comprised between about 100° C. and about 250° C.

18. The process of claim 1, wherein step (i) comprises heating at a temperature comprised between about 150° C. and about 220° C.

19. The process of claim 1, wherein step (i) comprises heating for a period of less than 10 hours.

20. The process of claim 1, wherein step (i) comprises heating for a period of less than 4 hours.

21. The process of claim 1, wherein step (i) comprises heating for a period of less than 1 hour.

22. The process of claim 1, wherein the complex is selected from pyridine-sulfur trioxide, trimethylamine-sulfur trioxide and triethylamine-sulfur trioxide complexes.

23. The process of claim 4, wherein the chlorinating agent in step (ii) is selected from $PCl_5$, $POCl_3$, $SOCl_2$, $ClSO_3H$, $COCl_2$, $ClCOCOCl$, sulfur chlorides, cyanuric chloride, acetyl chloride, trifluoroacetyl chloride, methanesulfonyl chloride, trifluoromethanesulfonyl chloride, benzoyl chloride, (trichloromethyl)benzene, benzenesulfonyl chloride, and toluenesulfonyl chloride.

24. The process of claim 4, wherein the chlorinating agent in step (ii) is selected from $SOCl_2$, $COCl_2$, and $ClCOCOCl$.

25. The process of claim 5, wherein the fluorinating agent is ammonium, sodium, potassium, or cesium fluoride or hydrogen difluoride.

26. The process of claim 5, wherein the fluorinating agent is pyridinium or triethylammonium polyhydrofluorides.

27. The process of claim 5, wherein the fluorinating agent is KF or $KHF_2$.

28. The process of claim 6, wherein the fluorinating agent is selected from $PF_5$, $POF_3$, $SOF_2$, $FSO_3H$, $COF_2$, FCOCOF, organic and inorganic hexafluorophosphates, hexafluorosilicates, tetrafluoroborates, sulfur tetrafluoride and its organic derivatives, cyanuric fluoride, acetyl fluoride, trifluoroacetyl fluoride, methanesulfonyl fluoride, trifluoromethanesulfonyl fluoride, benzoyl fluoride, (trifluoromethyl)benzene, benzenesulfonyl fluoride, and toluenesulfonyl fluoride.

29. The process of claim 6, wherein the fluorinating agent is selected from diethylaminosulfur trifluoride (DAST) and morpholinosulfur trifluoride.

30. The process of claim 9, wherein R¹ is $(M^{n+})_{1/n}$ and M is selected from Li, Na, K, Rb, Cs, Be, Mg, Ca, Sr, and Ba, and n is 1 or 2.

* * * * *